United States Patent
Konishi et al.

(10) Patent No.: US 11,358,123 B2
(45) Date of Patent: Jun. 14, 2022

(54) METHOD FOR RECYCLING SUPERABSORBENT POLYMER DERIVED FROM USED ABSORBENT ARTICLE AND RECYCLED SUPERABSORBENT POLYMER DERIVED FROM USED ABSORBENT ARTICLE

(71) Applicant: UNICHARM CORPORATION, Ehime (JP)

(72) Inventors: Takayoshi Konishi, Kagawa (JP); Takashi Kato, Kagawa (JP); Kouichi Yamaki, Kagawa (JP); Noritomo Kurita, Kagawa (JP)

(73) Assignee: Unicharm Corporation, Ehime (JP)

( * ) Notice: Subject to any disclaimer, the term of this patent is extended or adjusted under 35 U.S.C. 154(b) by 0 days.

(21) Appl. No.: 17/527,451

(22) Filed: Nov. 16, 2021

(65) Prior Publication Data
US 2022/0072511 A1 Mar. 10, 2022

Related U.S. Application Data

(63) Continuation of application No. PCT/JP2020/013840, filed on Mar. 26, 2020.

(30) Foreign Application Priority Data

May 30, 2019 (JP) .................................. 2019-101495
Oct. 31, 2019 (JP) .............................. JP2019-199172

(51) Int. Cl.
*B01J 20/34* (2006.01)
*B01J 20/26* (2006.01)

(52) U.S. Cl.
CPC ........... *B01J 20/3425* (2013.01); *B01J 20/26* (2013.01); *B01J 20/3475* (2013.01); *B01J 2220/68* (2013.01)

(58) Field of Classification Search
CPC ........ B01J 20/34; B01J 20/3425; B01J 20/26; B01J 20/3475; B01J 2220/68
USPC ........................................................... 502/25
See application file for complete search history.

(56) References Cited

U.S. PATENT DOCUMENTS

| | | | |
|---|---|---|---|
| 5,087,656 | A | 2/1992 | Yoshinaga et al. |
| 6,348,257 | B1 | 2/2002 | Koike et al. |
| 2015/0045461 | A1 | 2/2015 | Funamizu et al. |
| 2018/0236692 | A1 | 8/2018 | Lee et al. |
| 2021/0039072 | A1 | 2/2021 | Ito et al. |

FOREIGN PATENT DOCUMENTS

| | | |
|---|---|---|
| JP | H2-238035 A | 9/1990 |
| JP | H10-120921 A | 5/1998 |
| JP | 2003-326161 A | 11/2003 |
| JP | 2015-004034 A | 1/2015 |
| JP | 5996226 B2 | 9/2016 |
| WO | 2013/141357 A1 | 9/2013 |
| WO | 2019/087485 A1 | 5/2019 |
| WO | 2019/151538 A1 | 8/2019 |

OTHER PUBLICATIONS

International Search Report issued in corresponding International Application No. PCT/JP2020/013840, dated Jun. 16, 2020 (10 pages).

Written Opinion issued in corresponding International Application No. PCT/JP2020/013840, dated Jun. 16, 2020 (6 pages).

*Primary Examiner* — Edward M Johnson
(74) *Attorney, Agent, or Firm* — Osha Bergman Watanabe & Burton LLP

(57) ABSTRACT

A method of recycling superabsorbent polymers derived from a used absorbent article, the method including: treating the superabsorbent polymers with ozone water after inactivation; reactivating, with an alkaline aqueous solution, the superabsorbent polymers treated with the ozone water; and adding hydrophilic fine particles to the superabsorbent polymers reactivated with the alkaline aqueous solution and then drying the superabsorbent polymers.

11 Claims, 4 Drawing Sheets

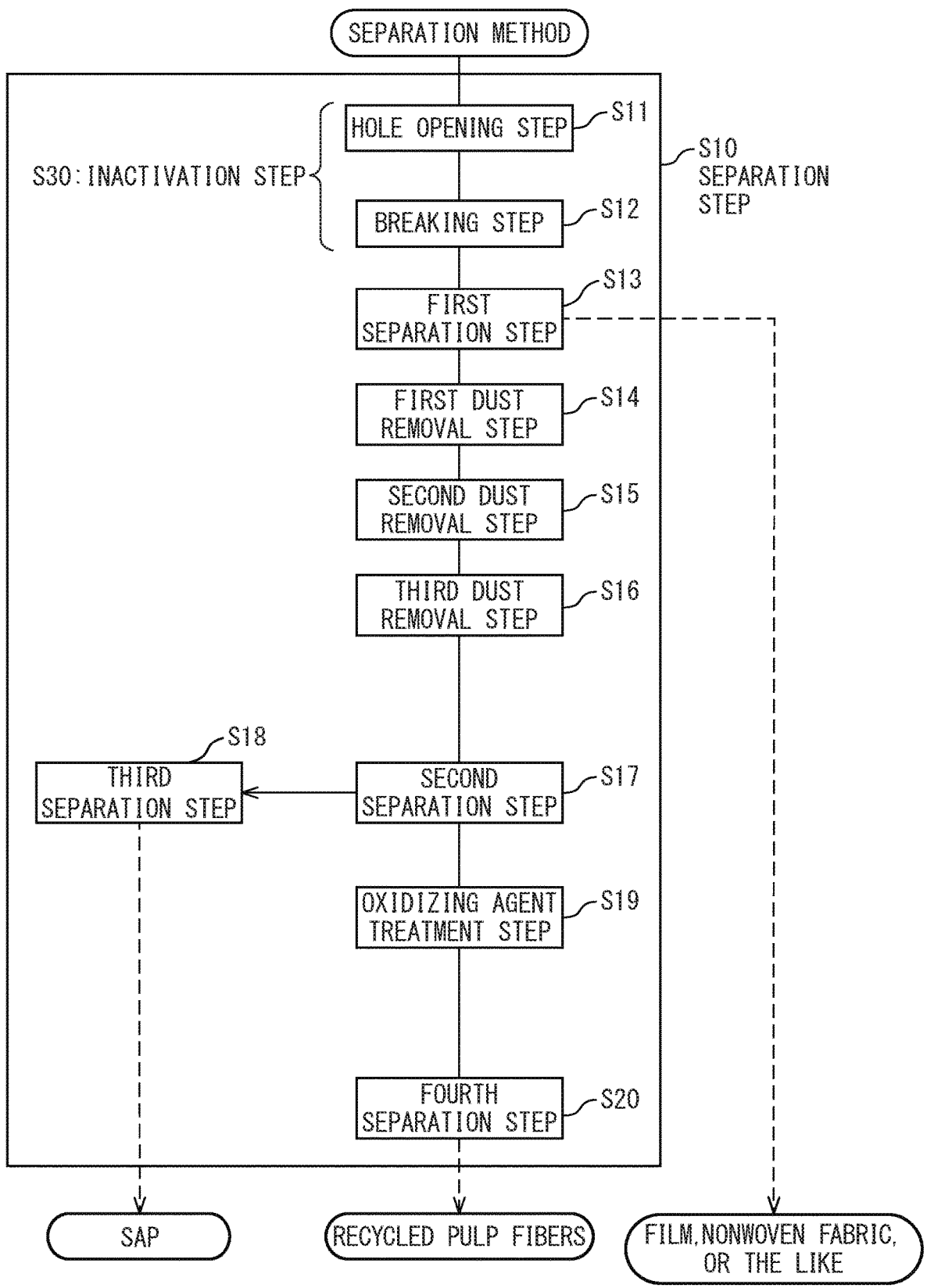

METHOD FOR RECYCLING SUPERABSORBENT POLYMER DERIVED FROM USED ABSORBENT ARTICLE AND RECYCLED SUPERABSORBENT POLYMER DERIVED FROM USED ABSORBENT ARTICLE

BACKGROUND

Technical Field

The present invention relates to a method of recycling superabsorbent polymers derived from a used absorbent article and recycled superabsorbent polymers derived from a used absorbent article.

Description of Related Art

Methods of recycling superabsorbent polymers derived from used absorbent articles are known. For example, Patent Literature 1 discloses a method of recycling used superabsorbent polymers. This method includes a step of treating used superabsorbent polymers with an aqueous solution of a polyvalent metal salt and a step of treating the superabsorbent polymers treated with the aqueous solution of a polyvalent metal salt with an aqueous solution of an alkali metal salt to desorb polyvalent metal ions from the superabsorbent polymers and restore the moisture absorption capability of the superabsorbent polymers.

PATENT LITERATURE

[Patent Literature 1] Japanese Patent No. 5996226

SUMMARY

However, according to the inventors' studies, in the method described in Patent Literature 1, there is a risk that the absorption performance of the recycled superabsorbent polymers, that is, the recycled superabsorbent polymers, may become poor compared with unused superabsorbent polymers. The reason therefor is as follows.

For example, when a foreign matter such as the material of the used absorbent article or excrement or dirt is attached to the surfaces of the superabsorbent polymers derived from the used absorbent article, there is a risk that absorption inhibition may occur in the recycled superabsorbent polymers due to this foreign matter or the like. Here, the method described in Patent Literature 1 may include a step of washing the superabsorbent polymers with water after the step of treating the superabsorbent polymers with the aqueous solution of an alkali metal salt. Therefore, there is a possibility that the foreign matter or the like may be removed by this washing. However, in such a case, since the reactivated superabsorbent polymers are washed with water, there is a risk that the superabsorbent polymers may absorb the washing water and swells. In such a case, when the superabsorbent polymers are dried afterward, a large amount of drying energy becomes necessary, and thus silica particles originally attached to the surfaces of the superabsorbent polymers in order to control hydrophilicity are likely to detach. When silica particles detach, it is likely that the water absorption time of the recycled superabsorbent polymers increases and the water absorption ratio decreases.

Furthermore, generally, since the manufacturers or types of used absorbent articles to be recovered are of great variety, at the time of recycling superabsorbent polymers derived from used absorbent articles, a plurality of types of superabsorbent polymers are mixed. In such a case, there is a possibility that the amount of originally attached silica particles or the degree of detachment of the silica particles may differ depending on the types of the superabsorbent polymers, and thus the water absorption times or water absorption ratios of recycled superabsorbent polymers are likely to vary. Due to that, for the recycled superabsorbent polymers as a whole, the water absorption time is likely to become long, and the water absorption ratio is likely to decrease.

One or more embodiments of the present invention provide a method of recycling superabsorbent polymers derived from a used absorbent article, capable of suppressing a relative decrease in the absorption performance of the recycled superabsorbent polymers, and to provide recycled superabsorbent polymers derived from a used absorbent article, in which a relative decrease in the absorption performance is suppressed.

One or more embodiments of the present invention are directed to a method of recycling superabsorbent polymers derived from a used absorbent article, the methods each comprising: an ozone treatment step of treating the superabsorbent polymers with ozone water after inactivation; a reactivation step of reactivating the superabsorbent polymers treated with the ozone water with an alkaline aqueous solution; and a surface treatment step of adding hydrophilic fine particles to the superabsorbent polymers reactivated with the alkaline aqueous solution and then drying the superabsorbent polymers.

One or more embodiments of the present invention are directed to recycled superabsorbent polymers derived from a used absorbent article, in which 2 to 10 mass % of silica fine particles are included and a water absorption ratio is 50 times or more. In addition, one or more embodiments of the present invention are directed to recycled superabsorbent polymers derived from a used absorbent article, in which 2 to 10 mass % of silica fine particles are included and a water retention ratio is 35 times or more. In addition, one or more embodiments of the present invention are directed to recycled superabsorbent polymers derived from a used absorbent article, in which 2 to 10 mass % of silica fine particles are included and an absorption time is 40 seconds or less. In addition, one or more embodiments of the present invention are directed to recycled superabsorbent polymers derived from a used absorbent article, in which 2 to 10 mass % of silica fine particles are included, a whiteness W is 80 or more, a whiteness WB is 60 or more, and a yellowness YI is 20 or less.

One or more embodiments of the present invention provide a method of recycling superabsorbent polymers derived from a used absorbent, capable of suppressing a relative decrease in the absorption performance of the recycled superabsorbent polymers, and to provide recycled superabsorbent polymers derived from a used absorbent article, in which a relative decrease in the absorption performance is suppressed.

BRIEF DESCRIPTION OF THE DRAWINGS

FIG. 4 is a flow chart illustrating an example of a method of extracting superabsorbent polymers to be recycled according to one or more embodiments.

DETAILED DESCRIPTION

Figure 1:
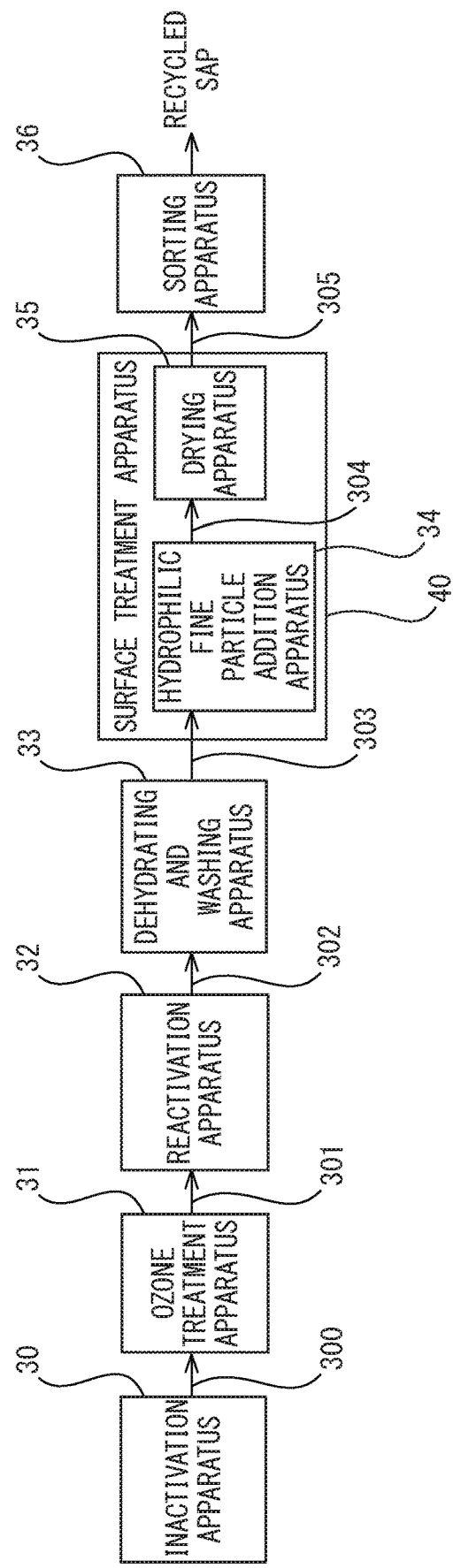
FIG. 1 is a block diagram illustrating a configuration example of a system that is used in a method of recycling superabsorbent polymers according to one or more embodiments.

One or more embodiments relate to the following aspects.

[Aspect 1]

A method of recycling superabsorbent polymers derived from a used absorbent article, the method comprising: an ozone treatment step of treating the superabsorbent polymers with ozone water after inactivation; a reactivation step of reactivating the superabsorbent polymers treated with the ozone water with an alkaline aqueous solution; and a surface treatment step of adding hydrophilic fine particles to the superabsorbent polymers reactivated with the alkaline aqueous solution and then drying the superabsorbent polymers.

In the present method, the inactivated superabsorbent polymers are treated with ozone water, which makes it possible to oxidatively decompose and remove a foreign matter or dirt attached to the surfaces of the superabsorbent polymers. This makes it possible to easily reactivate the superabsorbent polymers with an alkaline aqueous solution (for example, an aqueous solution of sodium hydroxide) while preventing the superabsorbent polymers from being impaired by a foreign matter or the like. Along with that, hydrophilic fine particles (for example, silica fine particles) can be spread and attached to the surfaces of the superabsorbent polymers almost entirely while preventing the superabsorbent polymers from being impaired by a foreign matter or the like. As described above, in the present method, the superabsorbent polymers can be easily reactivated, and the hydrophilic fine particles can be easily attached to the surfaces of the superabsorbent polymers. This makes it possible to suppress a relative decrease in the absorption performance of the recycled superabsorbent polymers.

[Aspect 2]

The method according to aspect 1, further comprising: a step of dehydrating and washing the superabsorbent polymers with an organic solvent after the reactivation step and before the addition of the hydrophilic fine particles to the superabsorbent polymers in the surface treatment step.

In the present method, after the reactivation step and before the addition of the hydrophilic fine particles in the surface treatment step, the superabsorbent polymers are dehydrated and washed with an organic solvent. Therefore, the amount of moisture in the vicinity of the surfaces of the superabsorbent polymers can be made almost constant, and thus the hydrophilic fine particles can be relatively uniformly added and dried on the surfaces of the superabsorbent polymers. This makes it possible to arrange the hydrophilic fine particles relatively uniformly on the surfaces of the superabsorbent polymers, makes it possible to make the absorption performance of the superabsorbent polymers relatively uniform, and, as a result, makes it possible to suppress a relative decrease in the absorption performance.

[Aspect 3]

The method according to aspect 1, wherein the reactivation step includes a step of dehydrating and washing the superabsorbent polymers while reactivating the superabsorbent polymers with an aqueous solution containing an alkali metal ion supply source capable of supplying an alkali metal ion and an organic solvent.

The present method includes a step of dehydrating and washing the superabsorbent polymers while reactivating the superabsorbent polymers with an aqueous solution containing an alkali metal ion supply source capable of supplying an alkali metal ion and an organic solvent. That is, in the present method, the reactivation step of reactivating the superabsorbent polymers with the alkaline aqueous solution, and the dehydrating and washing step of dehydrating and washing the superabsorbent polymers with the organic solvent are performed at the same time. Therefore, at the time of reactivating (neutralizing) the superabsorbent polymers, the superabsorbent polymers do not absorb water and swell, but is dehydrated, which makes it possible to decrease the volume of the superabsorbent polymers to be reactivated and thus makes it possible to efficiently reactivate the superabsorbent polymers. In addition, the reactivation treatment can be performed on the superabsorbent polymers while the strength of a gel remains strong, which makes it possible to suppress the breakage of the gel due to stirring or the like during the reactivation treatment. In addition, there is no need to increase the sizes of facilities for reactivation or dehydrating and washing, and the amount of the organic solvent used can be reduced. Furthermore, since the amount of moisture in the vicinity of the surfaces of the superabsorbent polymers can be made almost constant by the dehydrating, the hydrophilic fine particles can be added and dried relatively uniformly on the surface of the superabsorbent polymers. This makes it possible to arrange the hydrophilic fine particles relatively uniformly on the surfaces of the superabsorbent polymers, makes it possible to make the absorption performance of the superabsorbent polymers relatively uniform, and, as a result, makes it possible to suppress a relative decrease in the absorption performance.

[Aspect 4]

The method according to any one of aspects 1 to 3, further comprising: an inactivation step of inactivating the superabsorbent polymers with an inactivating agent, wherein in the ozone treatment step, the superabsorbent polymers inactivated with the inactivating agent is treated with the ozone water.

In the present method, the superabsorbent polymers are treated with the ozone water after being inactivated with an inactivating agent (for example, an acidic aqueous solution). Therefore, even when the inactivating agent remains on the surfaces of the superabsorbent polymers, the inactivating agent can be removed with the ozone water. This makes it possible to easily reactivate the superabsorbent polymers with the alkaline aqueous solution while preventing the superabsorbent polymers from being impaired by the inactivating agent. This makes it possible to suppress a relative decrease in the absorption performance of the recycled superabsorbent polymers.

[Aspect 5]

The method according to aspect 4, wherein the inactivating agent contains an acidic aqueous solution.

In the present method, as the inactivating agent, a polyvalent metal is not used, but an acidic aqueous solution is used, which makes it possible to suppress the remaining of ash in the recycled superabsorbent polymers and thereby makes it possible to further suppress absorption inhibition. In addition, since the acidic aqueous solution as the inactivating agent makes it difficult for ozone in the ozone water to be deactivated, a foreign matter or dirt that is attached to the surfaces of the superabsorbent polymers can be removed more accurately.

[Aspect 6]

The method according to any one of aspects 1 to 5, wherein the hydrophilic fine particles include silica fine particles.

In the present method, since silica fine particles are used as the hydrophilic fine particles, the silica fine particles can be arranged relatively more uniformly on the surfaces of the superabsorbent polymers. This makes it possible to make the absorption performance of the superabsorbent polymers relatively more uniform.

[Aspect 7]

The method according to any one of aspects 1 to 6, wherein the alkaline aqueous solution includes Na ions or K ions.

In the present method, since the alkaline aqueous solution has Na ions or K ions, the superabsorbent polymers can be stably and safely reactivated. This makes it possible to further enhance the absorption performance of the superabsorbent polymers.

[Aspect 8]

The method according to any one of aspects 1 to 7, wherein the ozone treatment step includes a step of transporting the inactivated superabsorbent polymers and the ozone water to the reactivation step while mixing the superabsorbent polymers and the ozone water with a twin screw pump.

In the present method, the superabsorbent polymers and the ozone water are mixed with a twin screw pump. Therefore, during mixing, the shape of the superabsorbent polymers can be made hard to break, and the superabsorbent polymers can be made easy to be recycled to almost the original shape afterward. This makes it possible to suppress a relative decrease in the absorption performance of the recycled superabsorbent polymers.

[Aspect 9]

The method according to any one of aspects 1 to 8, wherein the reactivation step includes a step of supplying the superabsorbent polymers treated with the ozone water and the alkaline aqueous solution to a mixing tank of a mixer and rotating the mixing tank, thereby stirring the alkaline aqueous solution containing the superabsorbent polymers.

In the present method, the superabsorbent polymers and the alkaline aqueous solution are supplied into the rotating mixing tank. Therefore, during stirring, the shape of the superabsorbent polymers that has swollen again in the alkaline aqueous solution can be made hard to break, and the superabsorbent polymers can be made easy to be recycled to almost the original shape afterward. This makes it possible to suppress a relative decrease in the absorption performance of the recycled superabsorbent polymers.

[Aspect 10]

The method according to any one of aspects 1 to 9, wherein the surface treatment step includes a step of drying the superabsorbent polymers to which the hydrophilic fine particles have been added with a dryer with a paddle.

In the present method, since the superabsorbent polymers is dried with a dryer with a paddle (paddle dryer) while being stirred, the particles of the superabsorbent polymers being aggregated and becoming a mass can be suppressed. This makes it possible to suppress a relative decrease in the absorption performance of the recycled superabsorbent polymers. In addition, since the hydrophilic fine particles are added to the superabsorbent polymers, it becomes difficult for the superabsorbent polymers to be attached to a paddle blade of the dryer with a paddle, and the drying efficiency and the yield can be enhanced.

[Aspect 11]

The method according to any one of aspects 1 to 10, further comprising: a sorting step of sieving the superabsorbent polymers which have been dried by particle sizes.

In the present method, since a sorting step is provided, the particle sizes of the superabsorbent polymers can be made almost uniform. This makes it possible to make the absorption performance of the superabsorbent polymers almost uniform.

[Aspect 12]

Recycled superabsorbent polymers derived from a used absorbent article, the recycled superabsorbent polymers comprising: 2 to 10 mass % of silica fine particles, wherein a water absorption ratio is 50 times or more, a water retention ratio is 35 times or more, and an absorption time is 40 seconds or less.

The present recycled superabsorbent polymers are recycled superabsorbent polymers derived from a used absorbent article and have a water absorption ratio of 50 times or more, a water retention ratio of 35 times or more, and an absorption time of 40 seconds or less with a smaller number of silica fine particles (10 mass % or less). That is, absorption inhibition is suppressed by reduction of ash, and a relative decrease in the absorption performance of the recycled superabsorbent polymers can be suppressed.

[Aspect 13]

Recycled superabsorbent polymers derived from a used absorbent article, the recycled superabsorbent polymers containing: 2 to 10 mass % of silica fine particles, wherein a whiteness W is 80 or more, a whiteness WB is 60 or more, and a yellowness YI is 20 or less.

The present recycled superabsorbent polymers are recycled superabsorbent polymers derived from a used absorbent article and have a whiteness W of 80 or more, a whiteness WB of 60 or more, and a yellowness YI of 20 or less with a smaller number of silica fine particles (10 mass % or less), thus, contain a small amount of an impurity, and have been uniformly treated. This suppresses absorption inhibition by reduction of ash and makes it possible to suppress a relative decrease in the absorption performance of the recycled superabsorbent polymers.

Hereinafter, a method of recycling superabsorbent polymers derived from a used absorbent article or used absorbent articles, according to one or more embodiments will be described. In other words, the recycling method can be referred to as a method of producing recycled superabsorbent polymers. Here, the used absorbent article refers to an absorbent article used by a user and includes an absorbent article in a state of having absorbed and held user's excrement, an absorbent article that has been used but does not absorb and hold any excrement, or an absorbent article that has not been used, but discarded. Examples of the absorbent article include a paper diaper, an incontinence pad, a sanitary napkin, a bed sheet, and a pet sheet, and the absorbent article includes superabsorbent polymers and may include pulp fibers. The recycled superabsorbent polymers refer to superabsorbent polymers that are derived from a used absorbent article and are recovered from the used absorbent article and recycled. It should be noted that the method of producing recycled superabsorbent polymers derived from a used absorbent article according to one or more embodiments can also be referred to as a method of producing recycled pulp fibers derived from a used absorbent article, since pulp fibers are recovered and separated in the way together with the superabsorbent polymers and recycled pulp fibers that are reusable are produced.

First, a configuration example of the absorbent article will be described. The absorbent article includes a top sheet, a back sheet, and an absorbent body arranged between the top sheet and the back sheet. The size of the absorbent article is, for example, approximately 15 to 100 cm in length and 5 to 100 cm in width. It should be noted that the absorbent article may further include a different member that ordinary absorbent articles include, for example, a diffusion sheet, leakproof walls, side sheets, or the like.

Examples of a configuration member of the top sheet include a liquid-permeable nonwoven fabric, a synthetic resin film having a liquid-permeable hole, a composite sheet thereof, and the like. Examples of a configuration member of the back sheet include a liquid-impermeable nonwoven fabric, a liquid-impermeable synthetic resin film, and a composite sheet thereof. Examples of a configuration member of the diffusion sheet include a liquid-permeable nonwoven fabric. Examples of a configuration member of the leakproof wall or the side sheet include a liquid-impermeable nonwoven fabric, and the leakproof wall may include an elastic member such as rubber. The material of the nonwoven fabric or the synthetic resin film is not particularly limited as long as the material can be used for absorbent articles, and examples thereof include an olefin-based resin such as polyethylene or polypropylene, a polyamide-based resin such as 6-nylon or 6,6-nylon, a polyester-based resin such as polyethylene terephthalate (PET) or polybutylene terephthalate (PBT), and the like. As the material of the nonwoven fabric, natural fibers such as cotton or rayon may be used. In one or more embodiments, an absorbent article for which a film is used as the configuration member of the back sheet and a nonwoven fabric is used as the configuration member of the top sheet will be described as an example.

Examples of the configuration member of the absorbent body include absorbent body materials, that is, pulp fibers and superabsorbent polymers. The pulp fibers are not particularly limited as long as the pulp fibers can be used for absorbent articles, and examples thereof include cellulose-based fibers. Examples of the cellulose-based fibers include a wood pulp, a crosslinked pulp, a non-wood pulp, a recycled cellulose, a semi-synthetic cellulose, and the like. As the size of the pulp fiber, the average value of the long diameters of the fibers is, for example, several tens of micrometer and may be 20 to 40 μm, and the average value of the fiber lengths is, for example, several millimeters and may be 2 to 5 mm. The superabsorbent polymers (SAP) are not particularly limited as long as the superabsorbent polymers can be used for absorbent articles, and examples thereof include polyacrylate-based, polysulfonate-based, and maleic anhydride-based water-absorbent polymers. As the size of the (dried) superabsorbent polymers, the average value of the particle sizes is, for example, several hundred micrometers and may be 200 to 500 μm. The absorbent body may include a core wrap formed of a liquid-permeable sheet.

One surface and the other surface of the absorbent body are joined to the top sheet and the back sheet, respectively, via an adhesive. In a plan view, a portion (peripheral portion) of the top sheet which extends toward the outer side of the absorbent body so as to surround the absorbent body is joined to a portion (peripheral portion) of the back sheet which extends toward the outer side of the absorbent body so as to surround the absorbent body via an adhesive. Therefore, the absorbent body is wrapped inside the joined body of the top sheet and the back sheet. The adhesive is not particularly limited as long as the adhesive can be used for absorbent articles, and examples thereof include a hot-melt adhesive. Examples of the hot-melt adhesive include pressure-sensitive adhesives or heat-sensitive adhesives mainly containing rubber such as styrene-ethylene-butadiene-styrene, styrene-butadiene-styrene, or styrene-isoprene-styrene or mainly containing an olefin such as polyethylene.

Next, a method of recycling a superabsorbent polymers derived from a used absorbent article or used absorbent articles, according to one or more embodiments will be described.

Figure 2:
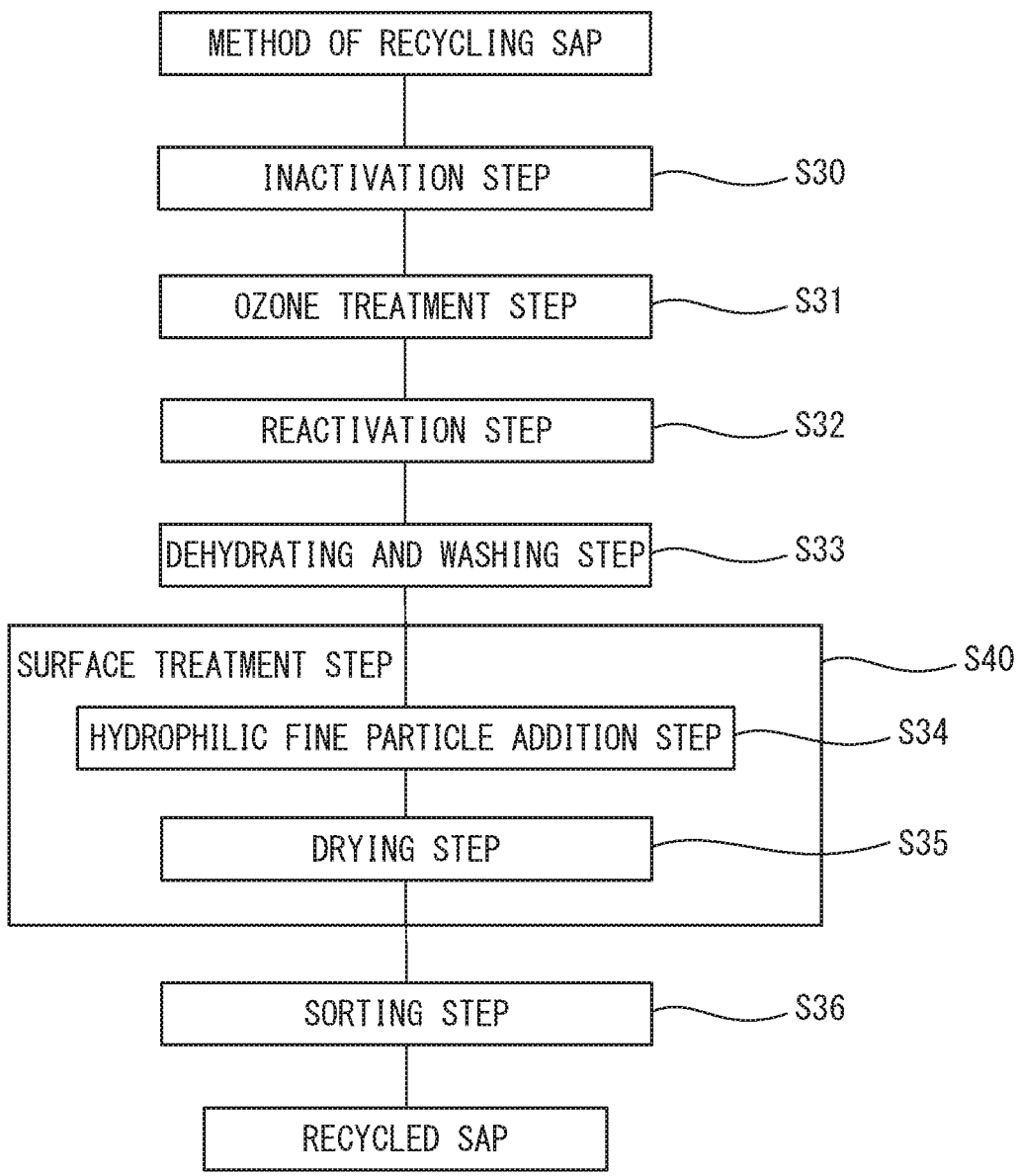
FIG. 2 is a flow chart illustrating an example of the method of recycling superabsorbent polymers according to one or more embodiments.

FIG. 1 is a block diagram illustrating a configuration example of a system 1 that is used in the method of recycling superabsorbent polymers derived from a used absorbent article according to one or more embodiments. FIG. 2 is a flow chart illustrating an example of the method of recycling superabsorbent polymers derived from a used absorbent article according to one or more embodiments.

The method of recycling a superabsorbent polymers derived from a used absorbent article includes an ozone treatment step S31, a reactivation step S32, and a surface treatment step S40 and may further include an inactivation step S30, a dehydrating and washing step S33, and/or a sorting step S36. In the recycling method, the surface treatment step S40 may include a hydrophilic fine particle addition step S34 and a drying step S35. Incidentally, the system 1 that is used in the method of recycling superabsorbent polymers derived from a used absorbent article includes an ozone treatment apparatus 31, a reactivation apparatus 32, and a surface treatment apparatus 40 and may further include an inactivation apparatus 30, a dehydrating and washing apparatus 33, and/or a sorting apparatus 36. In such a system 1, the surface treatment apparatus 40 may include a hydrophilic fine particle addition apparatus 34 and a drying apparatus 35. Hereinafter, each step will be specifically described.

The inactivation step S30 is executed with the inactivation apparatus 30. In the inactivation step S30, superabsorbent polymers derived from a used absorbent article or used absorbent articles are inactivated with an inactivating agent. In one or more embodiments, superabsorbent polymers extracted from a used absorbent article are immersed in an inactivation aqueous solution containing an inactivating agent, thereby forming an inactivated superabsorbent polymers 300. Examples of the inactivating agent include an acid. In such a case, the inactivation aqueous solution is an acidic aqueous solution.

The acid as the inactivating agent in the acidic aqueous solution is not particularly limited, and examples thereof include an inorganic acid and an organic acid. When the superabsorbent polymers are inactivated with an acid, it is difficult to leave ash in the superabsorbent polymers and the pulp fibers compared with a case where the superabsorbent polymers are inactivated with lime, calcium chloride, or the like. Examples of the inorganic acid include sulfuric acid, hydrochloric acid, and nitric acid, and sulfuric acid may be used from the viewpoint of not containing chlorine or the viewpoint of costs or the like. Examples of the organic acid include a carboxylic acid having a plurality of carboxyl groups (for example, citric acid, tartaric acid, malic acid, succinic acid, or oxalic acid), a carboxylic acid having one carboxyl group (for example, gluconic acid, pentanoic acid, butanoic acid, propionic acid, glycolic acid, acetic acid, or formic acid), a sulfonic acid (for example, methanesulfonic acid, trifluoromethanesulfonic acid, benzenesulfonic acid, or p-toluenesulfonic acid), and the like. As the organic acid, an organic acid having a plurality of carboxyl groups may be used, and citric acid may be used from the viewpoint of likelihood of forming a chelate complex with a divalent or higher metal (for example, calcium) contained in excrement or the like and a difficulty in leaving ash in the superabsorbent polymers and the pulp fiber. The citric acid concentration of the acidic aqueous solution is not particularly limited, but may be 0.5 to 4 mass %.

The acidic aqueous solution may have a predetermined pH. The upper limit of the predetermined pH is preferably 4.0, more preferably 3.5, and still more preferably 3.0. When the predetermined pH is too high, the superabsorbent polymers is not sufficiently inactivated, there is a tendency that discharge of excrement held by the superabsorbent polymers becomes insufficient, and there is a tendency that separation from the pulp fibers or the like becomes difficult. On the other hand, the lower limit of the predetermined pH is preferably 0.5 and more preferably 1.0. When the predetermined pH is too low, the superabsorbent polymers are further inactivated, and there is a tendency that a long time is taken for a reaction between the inactivated superabsorbent polymers and an alkaline aqueous solution in the reactivation step S32 (described below). In addition, when the predetermined pH is too low, in the case of recycling recycled pulp fibers in addition to recycling superabsorbent polymers derived from a used absorbent article, there is a risk that the recycled pulp fibers are damaged. It should be noted that, in the present specification, the pH means a value at 25° C. In addition, the pH can be measured using, for example, a twin pH meter AS-711 manufactured by HORIBA Co., Ltd. In the method of recycling superabsorbent polymers derived from a used absorbent article, the above-described predetermined pH may be satisfied at the end of the inactivation step S30. This is because the superabsorbent polymers are continuously left inactivated.

The specific configuration of the inactivation apparatus 30 that executes the inactivation step S30 is not particularly limited as long as the superabsorbent polymers derived from a used absorbent article can be immersed in the acidic aqueous solution. The inactivation apparatus 30 has, for example, a tank in which materials including the superabsorbent polymers can be arranged and the acidic aqueous solution can be stored. In the inactivation step S30, the materials including the superabsorbent polymers may be put into the tank after the acidic aqueous solution is stored in the tank or the acidic aqueous solution may be put into the tank after the materials including the superabsorbent polymers are arranged in the tank. The materials including the superabsorbent polymers are immersed in the acidic aqueous solution and an inactivation reaction is caused.

In the inactivation step S30, in order to evenly progress the reaction, while also depending on temperatures, the superabsorbent polymers can be inactivated by stirring the materials including the superabsorbent polymers (for example, the used absorbent article) in the tank containing the acidic aqueous solution for, for example, about 5 to 60 minutes. In the inactivation step S30, the temperature of the acidic aqueous solution is not particularly limited and is, for example, room temperature (25° C.), preferably a temperature higher than room temperature, more preferably 60° C. to 95° C., and still more preferably 70° C. to 90° C. This makes it easy to sterilize bacteria derived from excrement or the like that is contained in the acidic aqueous solution with the acid in the acidic aqueous solution.

In the end stage of the treatment of the inactivation step S30, the superabsorbent polymers 300 are not completely dehydrated, are in a state of having absorbed moisture, while not much (for example, a state of having absorbed water as much as about 10 times the volume of the superabsorbent polymers before the absorption of water), and is in a gel state.

It should be noted that, in a case where the materials to be immersed in the acidic aqueous solution includes, in addition to the superabsorbent polymers, different members such as pulp fibers, a liquid-permeable sheet, or a liquid-impermeable sheet, a separation step of separating and removing the members other than the superabsorbent polymers may be executed before or after the inactivation step S30. The separation step may be executed in parallel with the inactivation step S30 at the same time. Examples of the case where the materials to be immersed in the acidic aqueous solution includes, in addition to the superabsorbent polymers, different members includes a case where the materials are used absorbent articles containing the superabsorbent polymers. The separation step will be described below.

After that, the inactivated superabsorbent polymers are separated from the acidic aqueous solution (solid-liquid separation) with a sieve (or mesh) provided in the inactivation apparatus 30 and then supplied to the ozone treatment step S31 (ozone treatment apparatus 31) as the superabsorbent polymers 300.

The ozone treatment step S31 is executed with the ozone treatment apparatus 31. In the ozone treatment step S31, the inactivated superabsorbent polymers 300 are treated with ozone water. In one or more embodiments, the inactivated superabsorbent polymers 300 are brought into contact with (immersed in) ozone water containing a predetermined concentration of ozone for a predetermined time, thereby forming superabsorbent polymers 301 in which a foreign matter or the like on the surfaces of the superabsorbent polymers 300 has been removed with ozone.

To the surfaces of the superabsorbent polymers 300, bacteria or other organic matters derived from excrement in the used absorbent article are attached as a foreign matter or dirt. When the bacteria or the other organic matters remain on the surfaces, there is a risk that the absorption of the recycled superabsorbent polymers may be impaired. Therefore, in the ozone treatment step S31, the superabsorbent polymers 300 are substantially uniformly dispersed in the ozone water at a predetermined concentration (for example, 1 to 10 mass %), and bacteria or other organic matters attached to the surfaces of the superabsorbent polymers 300 are oxidatively decomposed and removed. That is, in the ozone treatment step S31, an impurity or an absorption-impairing substance attached to the surface of the superabsorbent polymers 300 is removed. In particular, sterilization with ozone water is referred to as bacteriolysis, and a chemical reaction between protein and ozone breaks the cell walls (membranes) of bacteria, and components in the cells leak, whereby the bacteria are killed. Therefore, the sterilization effect is significantly strong, the generation of resistant bacteria is unlikely, and the possibility of bacteria being propagated again after sterilization and covering the surfaces is extremely low.

At this time, when the superabsorbent polymers have been inactivated with the acidic aqueous solution (inactivation step S30), the inactivated superabsorbent polymers do not absorb water. Therefore, the superabsorbent polymers can be washed with ozone water having a low ozone concentration in an inactivated state, which makes it easy to remove bacteria and the like by washing and makes it possible to remove the bacteria and the like within a short period of time. In other words, the ozone treatment step S31 is preferably performed under an acidic condition and more preferably performed within a predetermined pH range, that is, 0.5 to 4.0, which is the same as the pH of the above-described acidic aqueous solution. Furthermore, since an odor component and a pigment component are also decomposed, the ozone treatment step S31 also has a deodorization and decolorization effect. It should be noted that, when the superabsorbent polymers 300 are treated with a gaseous substance, for example, ozone gas, since the superabsorbent polymers 300 are in a massive form (gel form), the inside of the mass is not properly treated, and it becomes difficult to uniformly treat the superabsorbent polymers as a whole. When the superabsorbent polymers are treated with ultraviolet rays or radioactive rays at a dose strong enough for the ultraviolet rays or radioactive rays to permeate the inside of the superabsorbent polymers, the superabsorbent polymers is decomposed. When the superabsorbent polymers are treated by heating or with high-pressure steam, dirt of excrement remains in the superabsorbent polymers. When the superabsorbent polymers are treated with an aqueous solution of sodium hypochlorite, since chlorine remains in the superabsorbent polymers, the superabsorbent polymers cannot be used as a sanitary material.

The ozone concentration in the ozone water is not particularly limited as long as bacteria, other organic matters, or the like attached to the surfaces of the superabsorbent polymers can be removed, but is preferably 0.3 to 2 ppm by mass and more preferably 0.5 to 1.5 ppm by mass. When the concentration is too low, the removal of bacteria or the like becomes difficult, and, when the concentration is too high, there is a risk that the superabsorbent polymers may begin to decompose. The contact time between the ozone water and the superabsorbent polymers is not particularly limited as long as bacteria, other organic matters, or the like attached to the surfaces of the superabsorbent polymers can be removed, but is set to be short when the ozone concentration in the ozone water is high and set to be long when the ozone concentration is low. The contact time is preferably 0.3 seconds to 15 minutes and more preferably 5 seconds to 10 minutes. The product of the ozone concentration (ppm) in the ozone water and the contact time (min) (hereinafter, also referred to as "CT value") is preferably 0.05 to 20 ppm·min and more preferably 0.08 to 10 ppm·min. When the CT value is too small, sterilization becomes difficult, and, when the CT value is too large, there is a risk that the superabsorbent polymers may decompose. Here, in the treatment with the ozone water, not only the removal of bacteria or the like but also bleaching can be performed by removing an impurity attached to the surface of the superabsorbent polymers 300. Examples of an ozone generation device that supplies ozone to water include ozone water exposure tester ED-OWX-2 manufactured by Ecodesign Co., Ltd., an ozone generation device OS-25V manufactured by Mitsubishi Electric Corporation, and the like.

In the ozone treatment step S31, in order to evenly progress the reaction, the ozone water containing the superabsorbent polymers 300 may be stirred in the tank. In the ozone treatment step S31, the temperature of the ozone water is not particularly limited and is, for example, room temperature (25° C.) and may be 10° C. to 40° C. When the temperature of the ozone water is set to be too high, ozone is likely to escape as gas and be deactivated, and, when the temperature is set to be too low, the time of the ozone treatment is likely to become long. This makes it easy to remove bacteria or organic matters attached to the surface of the superabsorbent polymers 300 with ozone in the ozone water.

It should be noted that, in the ozone treatment step S31, the ozone-containing ozone water is used, but a different oxidizing agent capable of removing an impurity attached to the surfaces of the superabsorbent polymers 300 may be jointly used with ozone or may be used singly. Examples of the oxidizing agent include hydrogen peroxide and peracetic acid.

The specific configuration of the ozone treatment apparatus 31 that executes the ozone treatment step S31 is not particularly limited as long as the inactivated superabsorbent polymers 300 can be brought into contact with (or immersed in) the ozone water without breaking the shape. Examples of the ozone treatment apparatus 31 include a twin screw pump (BQ-type: manufactured by Fukko Kinzoku Industry Co., Ltd.). The twin screw pump is a positive displacement self-priming pump. The twin screw pump includes a casing and twin screws that are arranged in a room in the casing and extending parallel to each other. The ozone water containing the superabsorbent polymers 300 is supplied to the room, reaches the twin screws in the radial direction, then, is extruded in the axial direction by the rotation of the twin screws, and discharged. In the stage of the treatment of the ozone treatment step S31, since the superabsorbent polymers 300 are in a state of a gel having absorbed moisture, while not much, as described above, it is difficult to stir the gel with a stirring blade in a manner that the gel does not break and to evenly progress the reaction. The twin screw pump may be used because the twin screw pump is capable of evenly mixing the inactivated superabsorbent polymers 300 with the ozone water without any stirring blades while rarely shearing the superabsorbent polymers 300 and thus not breaking the gel. In the ozone treatment step S31, the inactivated superabsorbent polymers 300 and the ozone water are mixed and reacted with each other with the twin screw pump.

After that, the ozone-treated superabsorbent polymers 300 are separated from the ozone water (solid-liquid separation) with a sieve (or mesh) provided in the ozone treatment apparatus 31 and then supplied to the reactivation step S32 (reactivation apparatus 32) as the superabsorbent polymers 301.

The reactivation step S32 is executed with the reactivation apparatus 32. In the reactivation step S32, the superabsorbent polymers 301 treated with ozone are reactivated with an alkaline aqueous solution. In one or more embodiments, the superabsorbent polymers 301 treated with ozone are neutralized by substituting H ions in the superabsorbent polymers with alkali metal ions to form reactivated superabsorbent polymers 302.

The superabsorbent polymers are inactivated with the acidic aqueous solution (inactivation step S30) and neutralized with the alkaline aqueous solution (reactivation step S32), whereby the superabsorbent polymers can be reactivated. Therefore, it is not necessary to use polyvalent metal ions as in Patent Literature 1, which makes it possible to suppress a situation where ash remains and absorption inhibition occurs.

The alkaline aqueous solution is an aqueous solution containing an alkali metal ion supply source capable of supplying alkali metal ions. Examples of the alkali metal ion include a lithium ion (Li ion), a sodium ion (Na ion), a potassium ion (K ion), and any combination thereof. The alkali metal ion supply source is not particularly limited as long as the alkali metal ion supply source is capable of supplying the above-described alkali metal ions, and examples thereof include a hydroxide of an alkali metal, a salt of a hydroxide of an alkali metal and an acid having a larger acid dissociation constant than an acid group in the superabsorbent polymers (hereinafter, also simply referred to as a "salt"), and the like. As the acid dissociation constant, a value described in Handbook on Electrochemistry edited by the Electrochemical Society of Japan can be employed.

Examples of the hydroxide of an alkali metal include lithium hydroxide, sodium hydroxide, potassium hydroxide, and any combinations thereof.

The salt can be an acidic salt or a basic salt. Examples of the hydroxide of an alkali metal in the salt include lithium hydroxide, sodium hydroxide, potassium hydroxide, and any combinations thereof. The acid in the salt is not particularly limited, and examples thereof include the acids exemplified in the inactivation step S30 (for example, hydrochloric acid and sulfuric acid), carbonic acid, and the like. Examples of the salt include lithium carbonate, sodium carbonate, potassium carbonate, lithium hydrogen carbonate, sodium hydrogen carbonate, potassium hydrogen carbonate, lithium chloride, sodium chloride, potassium chloride, and the like.

In the case of using the hydroxide of an alkali metal as the alkali metal ion supply source, the concentration of hydroxide ions of the alkaline aqueous solution is, for example, 0.1 to 5.0 mol/L, preferably 0.3 to 3.0 mol/L, and more preferably 0.4 to 1.0 mol/L.

The reactivation step S32 can be performed at a predetermined temperature, for example, 2 to 80° C., for a predetermined time, for example, 5 to 60 minutes. The reactivation step S32 may be neutral or alkaline and may be alkaline.

The specific configuration of the reactivation apparatus 32 that executes the reactivation step S32 is not particularly limited as long as the ozone-treated superabsorbent polymers 301 can be brought into contact with (or immersed in) the alkaline aqueous solution without breaking the shape. Examples of the reactivation apparatus 32 include a mixer (standard mixer NS-P-S manufactured by Tatechs). The mixer includes a rotatable mixing tank. The superabsorbent polymers 301 and the alkaline aqueous solution are supplied to the mixing tank and mixed by rotating the mixing tank. In the stage of the treatment of the reactivation step S32, since the superabsorbent polymers 301 are in a state of a gel having absorbed moisture, while not much, it is difficult to stir the gel with a stirring blade in a manner that the gel does not break and to evenly progress the reaction. This mixer may be used because the ozone-treated superabsorbent polymers 301 can be evenly mixed with the alkaline aqueous solution without any stirring blades by rotating the mixing tank while rarely shearing the superabsorbent polymers 301. In the reactivation step S32, the ozone-treated superabsorbent polymers 301 and the alkaline aqueous solution are mixed and reacted with each other with this mixer.

After that, the reactivated superabsorbent polymers 301 are separated from the alkaline aqueous solution (solid-liquid separation) with a sieve (or mesh) provided in the reactivation apparatus 32 and then supplied to the dehydrating and washing step S33 (dehydrating and washing apparatus 33) as the superabsorbent polymers 302.

The dehydrating and washing step S33 is executed with the dehydrating and washing apparatus 33. In the dehydrating and washing step S33, the reactivated superabsorbent polymers 302 are dehydrated and washed with an organic solvent. In one or more embodiments, the reactivated superabsorbent polymers 302 in a wet state are dehydrated while being washed with a hydrophilic organic solvent, thereby forming a dehydrated and washed superabsorbent polymers 303.

The organic solvent may be a hydrophilic organic solvent, and the hydrophilic organic solvent may be a solvent that is miscible with water. Examples of such an organic solvent include an alcohol-based solvent (for example, methanol, ethanol, propyl alcohol, an isomer thereof, butyl alcohol, and an isomer thereof), a ketone-based solvent (for example, acetone or methyl ethyl ketone), a nitrile-based solvent (for example, acetonitrile), and the like.

The organic solvent may contain a different solvent, for example, water as long as dehydrating is not affected. The proportion of the different solvent is less than 50 mass %, preferably 10 mass % or less, and more preferably 0 mass % with respect to the organic solvent.

In the dehydrating and washing step S33, the temperature of the dehydrating and washing is, for example, room temperature (for example, 25° C.) to 60° C. and may be 30° C. to 50° C. When the temperature becomes low, there is a tendency that a long time is taken for dehydrating or washing. When the temperature becomes high, the organic solvent is likely to evaporate, due to the evaporation, the concentration of the organic solvent decreases or the acid group of the superabsorbent polymers is dehydrated and condensed, and there are cases where the water-absorbing property of the superabsorbent polymers deteriorates. In the dehydrating and washing step S33, the time is, for example, 30 to 300 minutes.

The specific configuration of the dehydrating and washing apparatus 33 that executes the dehydrating and washing step S33 is not particularly limited as long as the reactivated superabsorbent polymers 302 can be brought into contact with (or immersed in) the organic solvent without breaking the shape. Examples of the dehydrating and washing apparatus 33 includes the same mixer as the reactivation apparatus 32 (standard mixer NS-P-S manufactured by Tatechs). The mixer may be used because the reactivated superabsorbent polymers 302 can be evenly mixed with the organic solvent without any stirring blades by rotating the mixing tank while rarely shearing the superabsorbent polymers 302. In the dehydrating and washing step S33, the reactivated superabsorbent polymers 302 and the organic solvent are mixed and reacted with each other with the mixer. The dehydrating and washing apparatus 33 and the reactivation apparatus 32 may be the same as each other.

At the end stage of the treatment of the dehydrating and washing step S33, the superabsorbent polymers 302 are significantly dehydrated to be in a state where, for example, the water absorption ratio is approximately twice and the superabsorbent polymers 302 becomes as smooth as sand.

Here, the reactivation step S32 may include a step of dehydrating and washing the superabsorbent polymers 301 while reactivating the superabsorbent polymers 301 with the aqueous solution containing an alkali metal ion supply source capable of supplying an alkali metal ion and the organic solvent and, in this case, the dehydrating and washing step S33 may not be performed. In other words, this method may include a step of performing the reactivation step S32 and the dehydrating and washing step S33 at the same time.

In the above-described aqueous solution, the proportion of the organic solvent with respect to the inactivated superabsorbent polymers 301 is once or more and 20 times or less, preferably twice or more and 10 times or less, and more preferably 4 times or more and 8 times or less the weight of the super absorbent polymers 301. When the amount of the organic solvent is too small, dehydrating does not easily progress, and, when the amount of the organic solvent is too large, the effect is saturated, and the cost increases. In addition, in the above-described aqueous solution, the concentration of the alkali metal ion supply source is 10 mmol/L or more and 200 mmol/L or less, preferably 20 mmol/L or more and 150 mmol/L or less, and more preferably 40 mmol/L or more and 100 mmol/L or less. When the amount of the alkali metal ion supply source is too small, reactivation does not easily progress, and, when the amount of the alkali metal ion supply source is too large, the effect is saturated, and the cost increases.

In a case where the reactivation step S32 and the dehydrating and washing step S33 are not performed at the same time, for example, the superabsorbent polymers 300 become 10 to 30 g/g after the inactivation step S30, the superabsorbent polymers 302 become 300 to 500 g/g after the reactivation step S32, and the superabsorbent polymers 303 become 5 to 20 g/g after the dehydrating and washing step S33. On the other hand, in a case where the reactivation step S32 and the dehydrating and washing step S33 are performed at the same time, for example, the superabsorbent polymers 300 become 10 to 30 g/g after the inactivation step S30, and the superabsorbent polymers 303 become 3 to 5 g/g after the reactivation step S32 and the dehydrating and washing step S33. As described above, at the time of reactivating the superabsorbent polymers 301, the volume of the superabsorbent polymers to be reactivated can be decreased by suppressing water absorption and swelling to dehydrate the superabsorbent polymers 301, and thus the reactivation can be efficiently performed.

The specific configuration of an apparatus that performs the reactivation step S32 and the dehydrating and washing step S33 at the same time is not particularly limited as long as the ozone-treated superabsorbent polymers 301 can be brought into contact with (or immersed in) the aqueous solution containing the alkali metal ion supply source and the organic solvent without breaking the shape. Examples of such an apparatus includes a mixer (standard mixer NS-P-S manufactured by Tatechs). The superabsorbent polymers 301 and the aqueous solution containing the alkali metal ion supply source and the organic solvent are supplied to the mixing tank and mixed by rotating the mixing tank, whereby the superabsorbent polymers 301 are dehydrated and washed while being reactivated.

The dehydrated and washed superabsorbent polymers 302 are separated from the organic solvent (solid-liquid separation) with a sieve (or mesh) provided in the dehydrating and washing apparatus 33 and then supplied to the hydrophilic fine particle addition step S34 (hydrophilic fine particle addition apparatus 34) as the superabsorbent polymers 303.

The surface treatment step S40 is executed with the surface treatment apparatus 40, and hydrophilic fine particles are added to the superabsorbent polymers 303 reactivated with the alkaline aqueous solution and dried. Hereinafter, the surface treatment step S40 will be described in detail.

The hydrophilic fine particle addition step S34 in the surface treatment step S40 is executed with the hydrophilic fine particle addition apparatus 34 in the surface treatment apparatus 40. In the hydrophilic fine particle addition step S34, hydrophilic fine particles are added to the dehydrated and washed superabsorbent polymers 303. In one or more embodiments, the hydrophilic fine particles are attached to the surfaces of the dehydrated and washed superabsorbent polymers 303.

As drying progresses in the drying step S35 or the like, the tackiness of the superabsorbent polymers increases, and the superabsorbent polymers are likely to be attached to the wall surfaces of the drying apparatus 35 or the superabsorbent polymers are likely to be aggregated to become a mass. In such a state, the hydrophilic fine particles are attached to the surfaces of the superabsorbent polymers, which makes it possible to reduce the increase in tackiness and makes it possible to suppress the attachment of the superabsorbent polymers to the wall surfaces or the aggregation of the superabsorbent polymers. Suppressing the aggregation of the superabsorbent polymers makes it possible to suppress a situation where the surface areas of the superabsorbent polymers decrease and the absorption performance of the superabsorbent polymers deteriorates. In addition, attaching the hydrophilic fine particles to the superabsorbent polymers that are wet immediately before the drying step S35 makes it easy for the hydrophilic fine particles to be attached to the surfaces of the superabsorbent polymers and makes it possible to suppress the detachment of the hydrophilic fine particles to the minimum extent. It should be noted that, when the amount is too large, there are cases that the absorption performance is affected.

Examples of the hydrophilic fine particles include hydrophilic metal oxides and complex oxides, and specific examples include silica (silicon oxide) fine particles, titania (titanium oxide) fine particles, alumina (aluminum oxide) fine particles, magnesia (magnesium oxide) fine particles, zirconia (zirconium oxide) fine particles, zinc oxide fine particles, zeolite fine particles, and combinations thereof. In one or more embodiments, silica fine particles may be used, and, as the silica fine particles, amorphous silica is preferable and fumed silica is more preferable.

The proportion of the hydrophilic fine particles with respect to the dry weight of the superabsorbent polymers is, for example, 1 to 15 mass %, preferably 2 to 10 mass %, and more preferably 3 to 6 mass %. The proportion of these hydrophilic fine particles is a value based on the amount charged. However, since the hydrophilic fine particles rarely remain in the hydrophilic fine particle addition apparatus 34 after the end of the hydrophilic fine particle addition step S34, it can be said that almost all the hydrophilic fine particles are actually added to the superabsorbent polymers.

It should be noted that, since the superabsorbent polymers before the hydrophilic fine particle addition step S34 rarely contains hydrophilic fine particles, as a result, the amount (proportion) of the hydrophilic fine particles charged can be referred to as the amount (proportion) of the hydrophilic fine particles that are actually contained in the superabsorbent polymers.

In the hydrophilic fine particle addition step S34, the temperature at the time of adding the hydrophilic fine particles is, for example, room temperature (for example, 25° C.) to 60° C. and may be 30° C. to 50° C. When the temperature becomes low, there is a tendency that it becomes difficult for the hydrophilic fine particles to be attached to the surface. When the temperature becomes high, it becomes easy for the organic solvent on the surface of the superabsorbent polymers to evaporate, the progress of the evaporation decreases the surface areas of the superabsorbent polymers at the time of attaching the hydrophilic fine particles, and there is a tendency that the amount of the hydrophilic fine particles being attached decreases. There are cases where the water-absorbing property of the recycled superabsorbent polymers deteriorates due to the excessive attachment of the hydrophilic fine particles to the surfaces of the superabsorbent recycled polymers. In the hydrophilic fine particle addition step S34, the time is, for example, 10 to 100 minutes.

The specific configuration of the hydrophilic fine particle addition apparatus 34 that executes the hydrophilic fine particle addition step S34 is not particularly limited as long as the hydrophilic fine particles can be attached to the surfaces of the dehydrated and washed superabsorbent polymers 303 without breaking their shapes. Examples of the hydrophilic fine particle addition apparatus 34 includes the same mixer as the dehydrating and washing apparatus 33 (standard mixer NS-P-S manufactured by Tatechs) and mixers of the same type as the above-described mixer that have a mixing tank with a small volume. The mixer may be used because the dehydrated and washed superabsorbent polymers 303 can be evenly mixed with the hydrophilic fine particles without any stirring blades by rotating the mixing tank while rarely shearing the superabsorbent polymers 303. In the hydrophilic fine particle addition step S34, with this mixer, the dehydrated and washed superabsorbent polymers 303 and the hydrophilic fine particles are mixed, and the hydrophilic fine particles are attached to the surfaces of the superabsorbent polymers 303.

After that, the superabsorbent polymers 303 including the hydrophilic fine particles attached to the surfaces are supplied to the drying step S35 (drying apparatus 35) as the superabsorbent polymers 304.

The drying step S35 in the surface treatment step S40 is executed with the drying apparatus 35 in the surface treatment apparatus 40. In the drying step S35, the superabsorbent polymers 304 including the hydrophilic fine particles attached to the surfaces are dried. In one or more embodiments, the superabsorbent polymers 304 are dried in a warming atmosphere while being stirred.

In the drying step S35, the drying temperature is, for example, room temperature (for example, 25° C.) to 150° C. and may be 70° C. to 120° C. When the drying temperature becomes low, there is a tendency that the drying time becomes long, and, when the drying temperature becomes high, there are cases where the water-absorbing property of the superabsorbent polymers deteriorates due to dehydrating condensation caused by the acid group of the superabsorbent polymers or the like. In the drying step S35, the drying time may be, for example, 30 to 300 minutes. The drying step S35 may be performed under reduced pressure, for example, at 0.1 to 100 kPa from the viewpoint of accelerating drying.

The specific configuration of the drying apparatus 35 that executes the drying step S35 is not particularly limited as long as the superabsorbent polymers 304 including the hydrophilic fine particles attached to the surface can be dried. Examples of the drying apparatus 35 include a dryer with paddles (paddle dryer NPD-1.6W-G manufactured by Nara Machinery Co., Ltd.). The dryer with paddles includes a casing and rotatable biaxial shafts that are arranged in a room in the casing and extend parallel to each other in the axial direction. Each shaft includes a wedge-shaped heat transfer blade (paddle blade) that broadens in the radial direction, and the paddle blades of both shafts overlap each other when seen in the axial direction. The superabsorbent polymers 304 including the hydrophilic fine particles attached to the surfaces are supplied to the room, receive a hot air, and are dried while being stirred with the paddle blades in a high-temperature atmosphere. In the drying step S35, the superabsorbent polymers 304 are dried in a warming atmosphere with the dryer with paddles while being stirred so as to prevent the superabsorbent polymers 304 from being attached to each other.

The drying step S35 may be performed so that the weight loss on drying of the superabsorbent polymers is 15% or less (2.0 g, 105° C., and 3 hours). This is because the use of the superabsorbent polymers is taken into account. The above-described weight loss on drying is measured according to "7. Loss on Drying Test" of <2. General Tests, Processes and Apparatus> of "The Japanese Specifications of Sanitary Napkin Materials" attached as an accompanying sheet to "Regarding The Japanese Specifications of Sanitary Napkin Materials" notified by Ministry of Health, Labour and Welfare as PFSB/ELD Notification No. 0325-(24) dated Mar. 25, 2015.

After that, the dried superabsorbent polymers 305 are supplied to the sorting step S36 (sorting apparatus 36) as the superabsorbent polymers 305.

The sorting step S36 is executed with the sorting apparatus 36. In the sorting step S36, the dried superabsorbent polymers 305 are sieved by particle sizes. In one or more embodiments, the dried superabsorbent polymers 305 are crushed (in a case where the superabsorbent polymers 305 have been fixed, integrated, or the like) and sieved by particle diameters and particle sizes, thereby generating superabsorbent polymers having optimal particle diameters for respective applications, that is, recycled superabsorbent polymers. As the sorting apparatus 36, an ordinary classifier can be used.

As described above, superabsorbent polymers derived from a used absorbent article or used absorbent articles are recycled to produce recycled superabsorbent polymers.

The produced recycled superabsorbent polymers contain 2 to 10 mass % of silica fine particles as described in examples below. The recycled superabsorbent polymers have a water absorption ratio of 50 times or more, a water retention ratio of 35 times or more, an absorption time of 40 seconds or lesser, a whiteness W of 80 or more, a whiteness WB of 60 or more, and a yellowness YI of 20 or less.

The method of recycling superabsorbent polymers derived from a used absorbent article according to one or more embodiments includes the ozone treatment step S31, the reactivation step S32, and the surface treatment step S40 as described above. In the ozone treatment step S31, the inactivated superabsorbent polymers are treated with the ozone water, which makes it possible to oxidatively decompose and remove a foreign matter or dirt attached to the surfaces of the superabsorbent polymers. This makes it possible to easily reactivate the superabsorbent polymers with the alkaline aqueous solution (for example, an aqueous solution of sodium hydroxide) while preventing the superabsorbent polymers from being impaired by a foreign matter or the like in the reactivation step S32. Along with that, the hydrophilic fine particles (for example, silica fine particles) can be spread and attached to the surfaces of the superabsorbent polymers almost entirely while preventing the superabsorbent polymers from being impaired by a foreign matter or the like in the surface treatment step S40. As described above, in the present method, the superabsorbent polymers can be easily reactivated, and the hydrophilic fine particles can be easily attached to the surfaces of the superabsorbent polymers. Such a synergistic effect makes it possible to suppress a relative decrease in the absorption performance of the recycled superabsorbent polymers.

In one or more embodiments, after the reactivation step S32 and before the addition of the hydrophilic fine particles to the superabsorbent polymers in the surface treatment step S40 (S34), the superabsorbent polymers are dehydrated and washed with the organic solvent (S33). Therefore, the amount of moisture in the vicinity of the surfaces of the superabsorbent polymers can be made almost constant, and thus the hydrophilic fine particles can be relatively uniformly added and dried on the surfaces of the superabsorbent polymers. This makes it possible to arrange the hydrophilic fine particles relatively uniformly on the surfaces of the superabsorbent polymers, makes it possible to make the absorption performance of the superabsorbent polymers relatively uniform, and, as a result, makes it possible to suppress a relative decrease in the absorption performance.

In one or more embodiments, the reactivation step S32 may include the step of dehydrating and washing the superabsorbent polymers while reactivating the superabsorbent polymers with the liquid mixture of the alkaline aqueous solution and the organic solvent. That is, the step of performing the reactivation step S32 and the dehydrating and washing step S33 at the same time may be included. In this case, at the time of reactivating (neutralizing) the superabsorbent polymers, the superabsorbent polymers do not absorb water and swell, but is dehydrated, which makes it possible to decrease the volume of the superabsorbent polymers to be reactivated and thus makes it possible to efficiently reactivate the superabsorbent polymers. In addition, the reactivation treatment can be performed on the superabsorbent polymers while the strength of a gel remains strong, which makes it possible to suppress the breakage of the gel due to stirring or the like during the reactivation treatment. In addition, there is no need to increase the sizes of facilities for reactivation or dehydrating and washing, and the amount of the organic solvent used can be reduced. Furthermore, since the amount of moisture in the vicinity of the surfaces of the superabsorbent polymers can be made almost constant by the dehydrating, the hydrophilic fine particles can be added and dried relatively uniformly on the surface of the superabsorbent polymers. This makes it possible to arrange the hydrophilic fine particles relatively uniformly on the surfaces of the superabsorbent polymers, makes it possible to make the absorption performance of the superabsorbent polymers relatively uniform, and, as a result, makes it possible to suppress a relative decrease in the absorption performance.

In one or more embodiments, the superabsorbent polymers are inactivated with the inactivating agent (for example, the acidic aqueous solution) (S30) and then treated with the ozone water (S31). Therefore, even when the inactivating agent remains on the surfaces of the superabsorbent polymers, the inactivating agent can be removed with the ozone water. This makes it possible to easily reactivate the superabsorbent polymers with the alkaline aqueous solution while preventing the superabsorbent polymers from being impaired by the inactivating agent in the reactivation step S32. This makes it possible to suppress a relative decrease in the absorption performance of the recycled superabsorbent polymers.

In one or more embodiments, at the time of inactivating the superabsorbent polymers (S30), as the inactivating agent, a polyvalent metal is not used, but the acidic aqueous solution is used. This makes it possible to suppress ash remaining in the recycled superabsorbent polymers and thereby makes it possible to further suppress absorption inhibition. In addition, since the acidic aqueous solution as the inactivating agent makes it difficult for ozone in the ozone water to be deactivated, a foreign matter or dirt that is attached to the surfaces of the superabsorbent polymers can be removed more accurately.

In one or more embodiments, in the hydrophilic fine particle addition step S34, since silica fine particles are used as the hydrophilic fine particles, the silica fine particles can be arranged relatively more uniformly on the surfaces of the superabsorbent polymers. This makes it possible to make the absorption performance of the superabsorbent polymers relatively more uniform.

In one or more embodiments, in the reactivation step S32, since the alkaline aqueous solution has Na ions or K ions, the superabsorbent polymers can be stably and safely reactivated. This makes it possible to further enhance the absorption performance of the superabsorbent polymers.

In one or more embodiments, in the ozone treatment step S31, the superabsorbent polymers and the ozone water are mixed with each other with the twin screw pump. Therefore, the shape of the gel-form superabsorbent polymers can be made hard to break during mixing, and the superabsorbent polymers can be made easy to be recycled to almost the original shape afterward. This makes it possible to suppress a relative decrease in the absorption performance of the recycled superabsorbent polymers.

In one or more embodiments, in the reactivation step S32, the superabsorbent polymers and the alkaline aqueous solution are supplied to the rotating mixing tank. Therefore, when the mixing tank is rotated to stir the superabsorbent polymers and the alkaline aqueous solution, the shape of the superabsorbent polymers that has swollen again in the alkaline aqueous solution can be made hard to break, and the superabsorbent polymers can be made easy to be recycled to almost the original shape afterward. This makes it possible to suppress a relative decrease in the absorption performance of the recycled superabsorbent polymers.

In one or more embodiments, in the surface treatment step S40, the superabsorbent polymers are dried with the dryer with paddles (paddle dryer) while being stirred (S35), which makes it possible to suppress the superabsorbent polymers being aggregated and becoming a mass. This makes it possible to suppress a relative decrease in the absorption performance of the recycled superabsorbent polymers. In addition, since the hydrophilic fine particles are attached to the surfaces of the superabsorbent polymers, it becomes difficult for the superabsorbent polymers to be attached to the paddle blades of the dryer with paddles, and the drying efficiency and the yield can be enhanced.

In one or more embodiments, since the sorting step of sieving the dried superabsorbent polymers by particle sizes is provided, the particle sizes of the superabsorbent polymers can be made almost uniform. This makes it possible to make the absorption performance of the superabsorbent polymers almost uniform.

Even though the recycled superabsorbent polymers of one or more embodiments are recycled superabsorbent polymers derived from a used absorbent article, they have a water absorption ratio of 50 times or more with a smaller number of silica fine particles (10 mass % or less). That is, absorption inhibition is suppressed by reduction of ash, which makes it possible to suppress a relative decrease in the absorption performance of the recycled superabsorbent polymers.

Even though the recycled superabsorbent polymers of one or more embodiments are recycled superabsorbent polymers derived from a used absorbent article, they have a water retention ratio of 35 times or more with a smaller number of silica fine particles (10 mass % or less). That is, absorption inhibition is suppressed by reduction of ash, which makes it possible to suppress a relative decrease in the absorption performance of the recycled superabsorbent polymers.

Even though the recycled superabsorbent polymers of one or more embodiments are a recycled superabsorbent polymers derived from a used absorbent article, they have an absorption time of 40 seconds or less with a smaller number of silica fine particles (10 mass % or less). That is, absorption inhibition is suppressed by reduction of ash, which makes it possible to suppress a relative decrease in the absorption performance of the recycled superabsorbent polymers.

Even though the recycled superabsorbent polymers of one or more embodiments are recycled superabsorbent polymers derived from a used absorbent article, they have a whiteness W of 80 or more, a whiteness WB of 60 or more, and a yellowness YI of 20 or less with a smaller number of silica fine particles (10 mass % or less), thus, contains a small amount of an impurity, and has been uniformly treated to have a high whiteness. This suppresses absorption inhibition by reduction of ash and makes it possible to suppress a relative decrease in the absorption performance of the recycled superabsorbent polymers.

It should be noted that, in the method of recycling a superabsorbent polymers derived from a used absorbent article according to one or more embodiments, the method of extracting the superabsorbent polymers from the used absorbent article is not particularly limited, and any method can be employed. As such a method, for example, a method shown below will be described with reference to FIG. 3 and FIG. 4.

Figure 3:
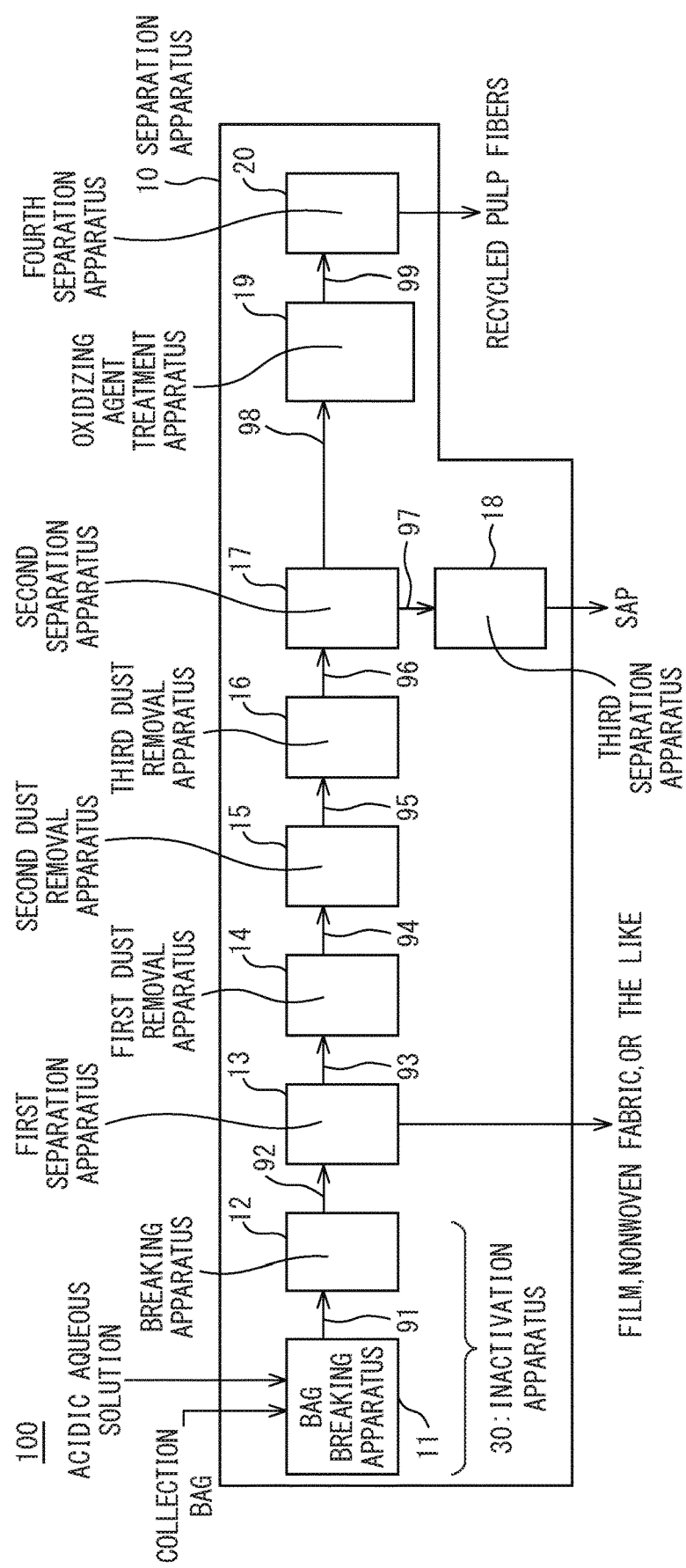
FIG. 3 is a block diagram illustrating a configuration example of an apparatus of extracting superabsorbent polymers to be recycled according to one or more embodiments.

FIG. 3 is a block diagram illustrating an example of a system 100 configured to separate a material from a used absorbent article according to one or more embodiments. The system 100 includes a separation apparatus 10 configured to separate a film and nonwoven fabric, superabsorbent polymers (SAP), and pulp fibers from a used absorbent article. Incidentally, FIG. 4 is a flow chart illustrating an example of a method of separating materials from a used absorbent article according to one or more embodiments. This method includes a separation step S10 of separating a film and nonwoven fabric, superabsorbent polymers (SAP), and pulp fibers from a used absorbent article. In addition, as shown in FIG. 3, the separation apparatus 10 includes a bag breaking apparatus 11 to a fourth separation apparatus 20, and accordingly, the separation step S10 includes a hole opening step S11 to a fourth separation step S20 as shown in FIG. 4. Hereinafter, each step will be specifically described.

It should be noted that, in one or more embodiments, a used absorbent article is recovered and acquired from the outside and is used for reuse (recycling). At that time, a plurality of the used absorbent articles are enclosed in a collection bag so that excrement, fungi, or odors do not leak to the outside. Each used absorbent article in the collection bag is recovered or the like in a state of being, mainly, rounded or folded such that the top sheet, onto which excrement has been excreted, faces inward so as to prevent, for example, the excrement or the fungi from being exposed toward the surface and the odors from diffusing toward the surrounding.

The hole opening step S11 is executed with the bag breaking apparatus 11. The bag breaking apparatus 11 includes a solution tank that stores an inactivation aqueous solution containing an inactivating agent and a bag breaking blade that rotates in the solution tank. The bag breaking apparatus 11 opens a hole in the collection bag put into the solution tank with the bag breaking blade in the inactivation aqueous solution. Thereby, a liquid mixture 91 of the collection bags into which the inactivating aqueous solution has intruded through the holes and the inactivating aqueous solution is generated. The inactivation aqueous solution inactivates the superabsorbent polymers in the used absorbent articles in the collection bag. Hereinafter, a case where an acidic aqueous solution is used as the inactivation aqueous solution will be described as an example. A breaking step S12 is executed with a breaking apparatus 12. The breaking apparatus 12 includes a biaxial breaker (for example, a biaxial rotary breaker). The breaking apparatus 12 breaks the collection bag including the used absorbent articles in the liquid mixture 91. Thereby, a liquid mixture 92 having broken matters from the collection bag including the used absorbent articles and the acidic aqueous solution is generated, and almost all the superabsorbent polymers in the used absorbent articles are inactivated. Here, the broken matters contain the pulp fibers, the superabsorbent polymers, and other materials (a film, a nonwoven fabric, the collection bag, and the like).

A first separation step S13 is executed with a first separation apparatus 13. The first separation apparatus 13 includes a pulper separator having a stirring and separating tank that functions as a washing tank and a sieving tank. The first separation apparatus 13 separates the pulp fibers, the superabsorbent polymers, excrement, and the acidic aqueous solution from the liquid mixture 92 while stirring the liquid mixture 92 and removing excrement and the like from the broken matters. Thereby, a liquid mixture 93 containing the pulp fibers, the superabsorbent polymers, the excrement, and the acidic aqueous solution is generated, and the films and nonwoven fabrics of the used absorbent articles, and the material of the collection bag and the like, are recovered.

It should be noted that, since the used absorbent articles are treated in the inactivation aqueous solution and the superabsorbent polymers are inactivated, the hole opening step S11 and the breaking step S12 (the bag breaking apparatus 11 and the breaking apparatus 12) can be referred to as the inactivation step S30 (inactivation apparatus 30). In addition, the breaking apparatus 12 may break the used absorbent articles in the collection bag in a gas (for example, in an air) instead of breaking the used absorbent articles in the inactivation aqueous solution. In such a case, the bag breaking apparatus 11 is not necessary. After the breaking, the broken matter and the inactivation aqueous solution in the breaking apparatus 12 are supplied to the first separation apparatus 13 (first separation step S13), and the superabsorbent polymers is inactivated. In such a case, the first separation apparatus 13 (first separation step S13) can be referred to as the inactivation step S30 (inactivation apparatus 30).

A first dust removal step S14 is executed with a first dust removal apparatus 14. The first dust removal apparatus 14 includes a screen separator and separates the liquid mixture 93 into the pulp fibers, the superabsorbent polymers, and the excrement in the acidic aqueous solution and other materials (foreign matters) with a screen. Thereby, a liquid mixture 94 containing the pulp fibers, the superabsorbent polymers, the excrement, and the acidic aqueous solution, which decreases in weight by the amount of the foreign matters, is generated, and the other materials are removed.

A second dust removal step S15 is executed with a second dust removal apparatus 15. The second dust removal apparatus 15 includes a screen separator and separates the liquid mixture 94 into the pulp fibers, the superabsorbent polymers, and the excrement in the acidic aqueous solution and other materials (small foreign matters) with a finer screen than the first dust removal apparatus 14. Thereby, a liquid mixture 95 containing the pulp fibers, the superabsorbent polymers, the excrement, and the acidic aqueous solution, which further decreases in weight by the amount of the foreign matters, is generated, and the other materials are further removed. A third dust removal step S16 is executed with a third dust removal apparatus 16. The third dust removal apparatus 16 includes a cyclone separator and separates the liquid mixture 95 into the pulp fibers, the superabsorbent polymers, and the excrement in the acidic aqueous solution and other materials (foreign matters having a heavy specific gravity) by centrifugal separation. Thereby, a liquid mixture 96 containing the pulp fibers, the superabsorbent polymers, the excrement, and the acidic aqueous solution, which further decreases in weight by the amount of the foreign matters, is generated, and the other materials having a large specific gravity are removed. It should be noted that, depending on the state of the liquid mixture 92 or the like (for example, the amount or size of the foreign matters), at least one of the first dust removal apparatus 14 through the third dust removal apparatus 16 may not be provided.

A second separation step S17 is executed with a second separation apparatus 17. The second separation apparatus 17 includes a drum screen separator and separates the liquid mixture 96 into the superabsorbent polymers in the acidic aqueous solution and the pulp fibers with a drum screen. Thereby, a liquid mixture 97 containing the superabsorbent polymers, the excrement, and the acidic aqueous solution is generated, and the pulp fibers are removed as a mixture 98. A third separation step S18 is executed with a third separation apparatus 18. The third separation apparatus 18 includes an inclined screen and separates the liquid mixture 97 into a solid containing the superabsorbent polymers and a liquid containing the excrement and the acidic aqueous solution with the screen. Thereby, superabsorbent polymers (SAP) are generated, and an acidic aqueous solution containing excrement or the like is removed.

An oxidizing agent treatment step S19 is executed with an oxidizing agent treatment apparatus 19. The oxidizing agent treatment apparatus 19 includes a treatment tank that stores an oxidizing agent aqueous solution and an oxidizing agent supply apparatus that supplies an oxidizing agent into the treatment tank. The oxidizing agent treatment apparatus 19 puts the mixture 98 into the treatment tank from the upper part or lower part of the treatment tank and mixes the mixture 98 with the oxidizing agent aqueous solution in the treatment tank. In addition, the oxidizing agent treatment apparatus 19 decomposes the superabsorbent polymers that are contained in the pulp fibers in the oxidizing agent aqueous solution with the oxidizing agent that is supplied from the lower part of the treatment tank with the oxidizing agent supply apparatus to solubilize the superabsorbent polymers in the oxidizing agent aqueous solution. Thereby, a liquid mixture 99 having the pulp fibers from which the superabsorbent polymers have been removed and the oxidizing agent aqueous solution containing a decomposition product of the superabsorbent polymers is generated. The oxidizing agent is an oxidizing agent capable of decomposing the superabsorbent polymers, examples thereof include ozone, and ozone may be used as having high sterilizing power or bleaching power.

The ozone concentration in the oxidizing agent aqueous solution may be 1 to 50 ppm by mass. When the concentration is too low, the superabsorbent polymers cannot be completely solubilized, and there is a risk that the superabsorbent polymers may remain in the pulp fibers. When the concentration is too high, there is a risk that the pulp fibers may be damaged. The treatment time with ozone is short when the ozone concentration in the oxidizing agent aqueous solution is high, and is long when the ozone concentration is low. The treatment time is typically 5 to 120 minutes. The product of the ozone concentration (ppm) in the oxidizing agent aqueous solution and the treatment time (minutes) (hereinafter, also referred to as "CT value") may be 100 to 6000 ppm·minute. When the CT value is too small, the superabsorbent polymers cannot be completely solubilized, and, when the CT value is too large, there is a risk that the pulp fibers may be damaged.

The fourth separation step S20 is executed with the fourth separation apparatus 20. The fourth separation apparatus 20 includes a screen separator and separates the liquid mixture 99 into the pulp fibers and the oxidizing agent aqueous solution with a screen. Thereby, pulp fibers are generated, and the oxidizing agent aqueous solution containing the decomposition product of the superabsorbent polymers is removed.

EXAMPLES

Hereinafter, embodiments of the present invention will be described based on examples, but the present invention is not limited to the examples.

(1) Raw Materials

As raw materials of superabsorbent polymers, two kinds of superabsorbent polymers (sample A and sample B) were prepared. The sample A was AQUA KEEP (manufactured by Sumitomo Seika Chemicals Co., Ltd., unused product) and manufactured by the reverse phase suspension polymerization method. The sample B was SANWET (manufactured by SDP Global Co., Ltd., unused product) and manufactured by the aqueous solution polymerization method. The water absorption ratio, water retention ratio, and water absorption time (Blank) of each sample are as shown in Table 1. It should be noted that methods for measuring the water absorption ratio, the water retention ratio, and the water absorption time will be described below.

TABLE 1

| Blank | | Sample A | Sample A + Sample B | Sample B |
|---|---|---|---|---|
| Water absorption ratio | g/g | 61.1 | 63.4 | 62.1 |
| Water retention ratio | g/g | 40.9 | 41.5 | 40.4 |
| Water absorption time | S | 33 | 34 | 32 |

(2) Addition of Silica Fine Particles (Hydrophilic Fine Particles)

The effect of the hydrophilic fine particle addition step S34 was evaluated for each case where the sample A, the sample B, or the sample A and the sample B was used as the superabsorbent polymers. Specifically, the effect was evaluated by the following method.

(2-1) Evaluation Method (a) 1 kg of the unused superabsorbent polymers were made to absorb a physiological saline solution (described below) as much as 40 times the superabsorbent polymers.

(b) The superabsorbent polymers that had absorbed the physiological saline solution was inactivated with an acidic aqueous solution (citric acid concentration: 1%) for 30 minutes.

(c) The inactivated superabsorbent polymers were immersed in ozone water (ozone concentration: 1 ppm) having a mass 10 times the mass of the superabsorbent polymers for 2 minutes.

(d) The ozone-treated superabsorbent polymers were neutralized with sodium hydroxide having a concentration of 0.4 mol/L for 30 minutes and reactivated.

(e) The reactivated superabsorbent polymers were immersed in methanol for 30 minutes.

(f) To the dehydrated and washed superabsorbent polymers, silica fine particles were added and mixed in a predetermined proportion (0 mass %, 1 mass %, 3 mass %, and 5 mass %) with respect to the dry weight of the superabsorbent polymers. Here, as the silica fine particles, hydrophilic fumed silica AEROSIL 150 (manufactured by Nippon Aerosil Co., Ltd.) was used.

(g) The superabsorbent polymers to which the silica fine particles had been added were dried at 105° C. for 60 minutes.

It should be noted that the steps (b) to (g) above correspond to S30 to S35 in the method of recycling superabsorbent polymers.

(h) For the obtained superabsorbent polymers, the water absorption ratio, the water retention ratio, and the water absorption time were measured. With the measurement values, the relationships between the indices of the measurement items and the proportions of the silica fine particles were evaluated for each superabsorbent polymers. The evaluation results are shown below in Table 2 (sample A), Table 3 (sample B), and Table 4 (sample A and sample B).

(Comparative Examples 1/3/5), an improvement effect was observed in the cases where the amount added was 1% or more (Comparative Examples 2/4/6) and the absorption performance became equal to or better than that of the virgin superabsorbent polymers (blank) in the cases where the amounts added were 3% and 5% (Examples 1, 2/3, 4, 8, 9/5, and 6). That is, it was confirmed that the water absorption ratio was 50 times or more, the water retention ratio was 35 times or more, and the absorption time was 40 seconds or shorter. In addition, it was found that the proportion of the hydrophilic fine particles with respect to the dry weight of the superabsorbent polymers may be 2 to 10 mass %. Furthermore, it was confirmed from the comparison between Example 4 and Example 7 with Example 8 that, even when the steps (d) and (e) were performed at the same time, the absorption performance was not affected and that the absorption performance became equal to or better than that of the virgin superabsorbent polymers (blank). It should be noted that, as described below, the effect of the ozone treatment of the step (c) on absorption performance appeared significantly, when superabsorbent polymers washed, separated, and recovered from a used diaper that had been actually used was used as the superabsorbent polymers. Therefore, in Example 8 and Example 9 in which superabsorbent polymers washed, separated, and recovered from a used diaper was not used, the absorption performances were almost the same.

TABLE 2

| Sample A | | Blank | Comparative Example 1 | Comparative Example 2 | Example 1 | Example 2 |
|---|---|---|---|---|---|---|
| Silica | % | — | 0% | 1% | 3% | 5% |
| Water absorption ratio | % | 61.1 | 64.6 | 60.4 | 60.9 | 60.3 |
| Water retention ratio | % | 40.9 | 41.4 | 38.3 | 40.5 | 42.0 |
| Water absorption time | Sec. | 33 | 194 | 98 | 33 | 25 |

TABLE 3

| Sample B | | Blank | Comparative Example 3 | Comparative Example 4 | Example 3 | Example 4 | Example 8 | Example 9 |
|---|---|---|---|---|---|---|---|---|
| Silica | % | — | 0% | 1% | 3% | 5% | 5% | 5% |
| Water absorption ratio | % | 62.1 | 62.0 | 62.4 | 61.5 | 62.8 | 62.6 | 66.3 |
| Water retention ratio | % | 40.4 | 40.1 | 39.6 | 41.0 | 39.6 | 42.4 | 40.1 |
| Water absorption time | Sec. | 32 | 57 | 44 | 26 | 17 | 18 | 20 |

TABLE 4

| Sample A + Sample B | | Blank | Comparative Example 5 | Comparative Example 6 | Example 5 | Example 6 |
|---|---|---|---|---|---|---|
| Silica | % | — | 0% | 1% | 3% | 5% |
| Water absorption ratio | % | 63.4 | 60.4 | 64.0 | 63.3 | 61.1 |
| Water retention ratio | % | 41.5 | 40.1 | 41.8 | 40.7 | 41.1 |
| Water absorption time | Sec. | 34 | 82 | 70 | 34 | 23 |

Here, Example 9 below is a sample obtained by performing the steps (d) and (e) at the same time. In addition, Example 8 below is a sample obtained by skipping the step (c).

(2-2) Evaluation Results

As for the water absorption time, as shown in Table 2 to Table 4, it was confirmed that, compared with the cases where the amount of the silica fine particles added was 0%

In addition, it was found that, even in a case where a plurality of kinds of superabsorbent polymers manufactured by different methods were present in a mixture form, that is, a case where the sample A and the sample B were present in a mixture form, as shown in Table 4, the same absorption performance as in the cases of homogeneous superabsorbent polymers (Examples 1 and 2/3 and 4) could be obtained by adjusting the amount of the silica fine particles added (Examples 5 and 6, and the like). In other words, it was found that, regardless of the method of manufacturing the superabsorbent polymers (for example, the reverse phase suspension polymerization method or the aqueous solution polymerization method), equal absorption performance can be obtained by the recycling method.

(3) Treatment with Ozone Water

The effect of the ozone treatment step S31 was evaluated for a case where the sample A recovered from a used diaper was used as the superabsorbent polymers. Specifically, the effect was evaluated by the following method.

(3-1) Evaluation Method

In the evaluation method (2-1), superabsorbent polymers washed, separated, and recovered from a used diaper that has been actually used was used as the superabsorbent polymers in step (a) (separation step S10), the condition of the presence or absence of the ozone treatment was evaluated with the condition of the presence or absence of the step (c), and the condition of the presence or absence of the addition of the silica fine particles was evaluated with the condition of the presence or absence of the step (f). Here, the amount of the silica fine particles added was fixed to 3 mass %. For the obtained superabsorbent polymers, the water absorption ratio, the water retention ratio, the water absorption time, the yellowness, and the whiteness were measured. With the measurement values, the relationships between the indices of the measurement items and the ozone treatment step S31 were evaluated. The evaluation results are shown below in Table 5. It should be noted that methods for measuring the yellowness and the whiteness will be described below.

(3-2) Evaluation Results

When the ozone treatment step S31 was not performed, regardless of the presence or absence of the addition of the silica fine particles, the water absorption ratio, the water retention ratio, and the water absorption time could not reach the level of the virgin superabsorbent polymers (blank) (Comparative Examples 7 and 8). On the other hand, when the ozone treatment step S31 was performed, the water absorption ratio, the water retention ratio, and the water absorption time became equal to the level of the virgin superabsorbent polymers by the addition of the silica fine particles (Example 7). From this fact, it was clarified by the ozone treatment step S31 that an absorption-impairing substance, which is hard to be removed by a method other than an oxidization treatment with ozone, is present on the surface of the superabsorbent polymers derived from a used absorbent article, the absorption inhibition substance can be removed with ozone, and the removal of the absorption inhibition substance makes the effect of the silica fine particles significantly appear and makes it possible to enhance the absorption performance of the superabsorbent polymers derived from a used absorbent article.

In addition, when the ozone treatment step S31 was not performed, regardless of the presence or absence of the addition of the silica fine particles, the yellowness (YI) was large (close to yellow) and the whiteness (W, WB) was small (not close to white) compared with the virgin superabsorbent polymers (blank) (Comparative Examples 7 and 8). On the other hand, when the ozone treatment step S31 was performed, the addition of the silica fine particles makes the yellowness (YI) as small (not close to yellow) and the whiteness (W, WB) as large (close to white) as the level of the virgin superabsorbent polymers (Example 7). From this fact, it was clarified by the ozone treatment step S31 that a tone-changing substance, which is hard to be removed by a method other than an oxidization treatment with ozone, is present on the surface of the superabsorbent polymers derived from a used absorbent article, the tone-changing substance can be removed with ozone, and the removal of the tone-changing substance makes it possible to enhance the whiteness of the superabsorbent polymers derived from a used absorbent article. In addition, it was found that, in a case where superabsorbent polymers derived from a used absorbent article include 2 to 10 mass % of silica fine particles, the whiteness W is 80 or more, the whiteness WB is 60 or more, and a yellowness YI is 20 or less.

<Absorption Time of Superabsorbent Polymers>

The absorption time (absorption rate) of the superabsorbent polymers is measured as follows.

(1) A test solution is put into a 1 liter beaker in advance and put into a water bath to adjust the liquid temperature of a physiological saline solution to 25° C.±1° C. (measured with a rod-shaped thermometer). Here, the physiological saline solution is an aqueous solution of 0.9% sodium chloride and is prepared as follows. A 3 L beaker is placed on an electronic balance (sensitivity: 0.001 g), the electronic balance is reset to 0, then, 27.0 g of sodium chloride (reagent, first grade) is put into the 3 L beaker, and ion exchange water is added thereto to adjust the weight to 3000.0 g. The components are stirred until dissolved.

(2) A rotor (30 mm×8 mmφ) is put into a 100-ml beaker.

(3) A 100 ml beaker is placed on the electronic balance, the electronic balance is reset to 0, and then 50 g of a physiological saline solution (adjusted to a liquid temperature of 25° C.) is put into the 100 ml beaker.

(4) The 100 ml beaker is placed on a magnetic stirrer (MAGMIX STIRRER (AC100W): manufactured by Mitamura Riken Kogyo Inc.), and the physiological saline solution is stirred with the rotor with the numerical value of the meter set to 600 rpm.

(5) The rotation speed of the rotor is actually measured with a non-contact type tachometer (TM-4000: manufactured by Line Seiki Co., Ltd.), and the rotation speed is adjusted to 600±30 rpm.

TABLE 5

| Sample A | | | Blank | Example 7 | Comparative Example 7 | Comparative Example 8 |
|---|---|---|---|---|---|---|
| Presence or absence of ozone treatment (S31)/ presence or absence of silica addition (S34) | | | —/— | Present/present | Absent/present | Absent/absent |
| Absorption performance | Water absorption ratio | % | 61.1 | 60.9 | 48.2 | 49.7 |
| | Water retention ratio | % | 40.9 | 40.5 | 33.8 | 34.6 |
| | Water absorption time | Sec. | 33 | 33 | 42 | 36 |
| Yellowness, whiteness | YI | | 10.3 | 13.8 | 28.3 | 29.4 |
| | W | | 91.3 | 88.4 | 73.0 | 71.9 |
| | WB | | 79.6 | 72.7 | 45.8 | 43.2 |

(6) 2.00 g of the superabsorbent polymers, which are measurement objects, are precisely weighed with the electronic balance.

(7) The superabsorbent polymers of (6) are put into the 100 ml beaker of (5), and a stopwatch is started at the same time.

(8) The stopwatch is stopped at a point in time when the liquid surface of the physiological saline solution containing the superabsorbent polymers in the 100 ml beaker becomes flat, which is an end point. Here, regarding the way of viewing the end point, a point in time when the slope of the vortex of the rotating physiological saline solution becomes close to a flat surface is regarded as the end point and is determined by observing the disappearance of light that is reflected on the liquid surface of the vortex.

(9) The time taken for the liquid surface to become flat from the putting of the superabsorbent polymers is regarded as the absorption time (unit: s (seconds: up to two decimal places)). The test is performed 5 times, and the average is finally regarded as the absorption time of the superabsorbent polymers.

<Water Absorption Ratio and Water Retention Ratio of Superabsorbent Polymers>

The water absorption ratio and the water retention ratio of the superabsorbent polymers are measured as follows.

(A) Measurement of Water Absorption Ratio (1) A bag including a sample is prepared.

First, the bag is prepared as follows. A rectangular nylon net (250-mesh nylon net (N-NO. 250HD: manufactured by NBC Meshtec Inc.) that is 200 mm in the longitudinal direction and 200 mm in the width direction is prepared. Next, the nylon mesh is folded at the central position in the width direction (a position at 100 mm) along a fold line that extends in the longitudinal direction. In addition, in the folded nylon net, heat sealing that extends in the longitudinal direction is performed at positions 5 mm inward from two widthwise end edges, respectively, and heat sealing that extends in the width direction is performed at a position 5 mm inward from one longitudinal end edge. A bag of the nylon net on which heat sealing has been performed along three sides is formed.

Next, the bag including the sample is prepared as follows. 1.000 g of the superabsorbent polymers, which are measurement objects, are accurately measured with an electronic balance (sensitivity: 0.001 g). Next, the weighed superabsorbent polymers are put into the bag of the nylon net. In addition, heat sealing is performed on one remaining side on which heat sealing is not performed in the bag of the nylon net.

(2) 1000 ml of a physiological saline solution is put into a 2 L beaker, and the liquid temperature is measured. . . . A The physiological saline solution is the same as that is used for the measurement of the absorption time of the superabsorbent polymers.

(3) The bag including the sample of (1) is immersed so as to touch the bottom of the 2 L beaker of (2). (4) One side in the upper part of the bag is fixed to the opening end of the 2 L beaker with a clothes-peg, and the bag is left to stand for 1 hour. At this time, the superabsorbent polymers and the nylon net are prevented from coming into close contact with each other as much as possible. (5) After having been left to stand, the bag is lifted, the center of a short side of the bag (5 mm from the top end and 50 mm from both ends) is clamped with washing scissors and drained for 15 minutes.

(6) The mass of the drained bag is measured with an electronic balance. . . . B (7) The water absorption ratio is calculated by the following formula. Water absorption ratio=B−2.6 (g/g)

The test is performed 5 times, and the average is finally regarded as the water absorption ratio of the superabsorbent polymers.

(B) Measurement of Water Retention Ratio (1) The drained bag of (A) (6) is dehydrated with a centrifuge (Type H130: manufactured by Kokusan Co., Ltd.). Here, the conditions are a rotation speed of 850 rpm (150 G), a time of 90 seconds after a certain period of 850 rpm.

(2) The mass of the dehydrated bag is measured with an electronic balance. . . . C (3) The water retention ratio is calculated by the following formula. Water absorption ratio=C−2.3 (g/g)

The test is performed 5 times, and the average is finally regarded as the water retention ratio of the superabsorbent polymers.

<Whiteness and Yellowness>

The whiteness and the yellowness are measured as follows.

(1) A sample was placed in a constant-temperature and constant-humidity chamber at a temperature of 20±5° C. and a humidity of 65±5% RH.

(2) The values of W, WB, and YI were measured with a flicker photometry type color difference meter (Z-300: Nippon Denshoku Industries Co., Ltd.).

Although the disclosure has been described with respect to only a limited number of embodiments, those skilled in the art, having benefit of this disclosure, will appreciate that various other embodiments may be devised without departing from the scope of the present disclosure. Accordingly, the scope of the invention should be limited only by the attached claims.

REFERENCE SIGNS LIST

S31 Ozone treatment step
S32 Reactivation step
S40 Surface treatment step

The invention claimed is:

1. A method of recycling superabsorbent polymers derived from a used absorbent article, the method comprising:
   treating the superabsorbent polymers with ozone water after inactivation;
   reactivating, with an alkaline aqueous solution, the superabsorbent polymers treated with the ozone water; and
   adding hydrophilic fine particles to the superabsorbent polymers reactivated with the alkaline aqueous solution and then drying the superabsorbent polymers.

2. The method according to claim 1, further comprising:
   after the reactivating of the superabsorbent polymers and before the adding of the hydrophilic fine particles, dehydrating and washing the superabsorbent polymers with an organic solvent.

3. The method according to claim 1, wherein
   the reactivating of the superabsorbent polymers includes:
   dehydrating and washing the superabsorbent polymers while reactivating the superabsorbent polymers with an aqueous solution containing an organic solvent and an alkali metal ion supply source supplying an alkali metal ion.

4. The method according to claim 1, further comprising:
inactivating the superabsorbent polymers with an inactivating agent, wherein
in the treating of the superabsorbent polymers, the superabsorbent polymers inactivated with the inactivating agent are treated with the ozone water.

5. The method according to claim 4, wherein
the inactivating agent contains an acidic aqueous solution.

6. The method according to claim 1, wherein
the hydrophilic fine particles include silica fine particles.

7. The method according to claim 1, wherein
the alkaline aqueous solution includes a Na ion or a K ion.

8. The method according to claim 1, wherein
the treating of the superabsorbent polymers includes:
transporting the superabsorbent polymers after the inactivation and the ozone water to the reactivating of the superabsorbent polymers while mixing the superabsorbent polymers and the ozone water with a twin screw pump.

9. The method according to claim 1, wherein
the reactivating of the superabsorbent polymers includes:

supplying the superabsorbent polymers treated with the ozone water and the alkaline aqueous solution to a mixing tank of a mixer, and stirring, by rotating the mixing tank, the alkaline aqueous solution containing the superabsorbent polymers.

10. The method according to claim 1, wherein
the adding of the hydrophilic fine particles includes:

drying, with a dryer with a paddle, the superabsorbent polymers to which the hydrophilic fine particles have been added.

11. The method according to claim 1, further comprising:

sieving, by particle sizes, the superabsorbent polymers which have been dried.

\* \* \* \* \*